United States Patent
Blye et al.

(10) Patent No.: US 10,351,587 B2
(45) Date of Patent: Jul. 16, 2019

(54) METHOD OF MAKING AND USING 7α, 11β-DIMETHYL-17β-HYDROXYESTR-4-EN-3-ONE 17-UNDECANOATE

(75) Inventors: Richard P. Blye, Highland, MD (US); Hyun K. Kim, Bellingham, WA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 16 days.

(21) Appl. No.: 13/022,391

(22) Filed: Feb. 7, 2011

(65) Prior Publication Data

US 2011/0195942 A1   Aug. 11, 2011

Related U.S. Application Data

(63) Continuation of application No. 12/184,600, filed on Aug. 1, 2008, now abandoned, which is a continuation of application No. 11/040,964, filed on Jan. 21, 2005, now abandoned, which is a continuation of application No. 10/260,854, filed on Sep. 30, 2002, now abandoned, which is a continuation of application No. PCT/US01/10293, filed on Mar. 30, 2001.

(60) Provisional application No. 60/194,440, filed on Apr. 4, 2000, provisional application No. 60/193,530, filed on Mar. 31, 2000.

(51) Int. Cl.
*A61K 31/56* (2006.01)
*C07J 1/00* (2006.01)
*C07J 21/00* (2006.01)
*C07J 71/00* (2006.01)

(52) U.S. Cl.
CPC ............ *C07J 1/0059* (2013.01); *A61K 31/56* (2013.01); *C07J 1/007* (2013.01); *C07J 1/0074* (2013.01); *C07J 21/006* (2013.01); *C07J 71/001* (2013.01)

(58) Field of Classification Search
CPC ......... A61K 31/56; C07J 1/0059; C07J 1/007; C07J 1/0074; C07J 21/006; C07J 71/001
USPC .......................................... 514/179; 552/647
See application file for complete search history.

(56) References Cited

U.S. PATENT DOCUMENTS

| 2,806,863 A | 9/1957 | Herr |
| 2,837,517 A | 6/1958 | Herr |
| 3,160,644 A | 12/1964 | Herr |
| 3,438,783 A | 4/1969 | Machlin |
| 3,577,410 A | 5/1971 | Teller et al. |
| 5,855,905 A | 1/1999 | Oettel et al. |
| 5,952,319 A | 9/1999 | Cook et al. |
| 6,313,108 B1 | 11/2001 | Loozen et al. |
| 6,492,536 B2 | 12/2002 | Bhatnagar et al. |
| 6,670,352 B2 | 12/2003 | Cook et al. |
| 2003/0130243 A1 | 7/2003 | Blye et al. |

FOREIGN PATENT DOCUMENTS

| CA | 943126 A1 | 3/1974 |
| DE | 2119708 | 11/1971 |
| EP | 957953 | 5/1964 |
| GB | 1341601 | 12/1973 |
| WO | WO 99/26962 A | 6/1999 |

OTHER PUBLICATIONS

"Rote Liste," *ECV Editio Cantor*, 1996.
"The Merck Index, 11th Edition," Merck & Co., Inc., 1989.
Balasubramanian et al., *Annual Reports in Medicinal Chemistry*, 33, 151-162 (1998).
Davidson et al., "Increasing Circulating Androgens with Oral Testosterone Undecanoate in Eugonadal Men," *Chemical Abstracts + Indexes American Chemical Society*, vol. 13, No. 107, p. 91; Sep. 28, 1987.
Draetta et al., *Annual Reports in Medicinal Chemistry*, 31, 241-248 (1996).

(Continued)

*Primary Examiner* — Barbara P Badio
(74) *Attorney, Agent, or Firm* — Leydig, Voit & Mayer, Ltd.

(57) ABSTRACT

Methods of using 7α,11β-dimethyl-17β-hydroxy-4-estren-3-one bucyclate (I) and 7α,11β-dimethyl-17β-hydroxyestr-4-en-3-one 17-undecanoate (II)

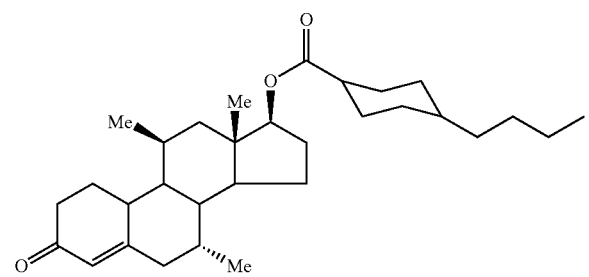

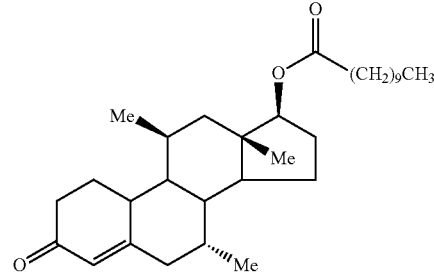

for various hormonal therapies, dosage forms comprising 7α,11β-dimethyl-17β-hydroxy-4-estren-3-one bucyclate and 7α,11β-dimethyl-17β-hydroxyestr-4-en-3-one 17-undecanoate, and processes for their preparation.

22 Claims, 16 Drawing Sheets

(56) References Cited

OTHER PUBLICATIONS

Monder et al., "Metabolism of Testosterone trans-4-n-butylcyclohexyl carboxylate, a high potency androgen, in rodents and primates: in vitro studies," *Journal of Endocrinology*, vol. 140, No. 3, pp. 465-473; 1994.
Monder et al., "Studies on the Metabolism of Testosterone Trans-4-n-butylcyclohexanoic Acid in the Cynomolgus Monkey, *Macaca fascicularis*," *Journal of Steroid Biochemistry and Molecular Biology*, vol. 50, No. 5-6, pp. 305-311; 1994.
Nieschlag et al., "Plasma Androgen Levels in Men After Oral Administration of Testosterone or Testosterone Undecanoate," *Acta Endocrinol*, vol. 79, No. 2, pp. 366-374; 1975.
Partsch et al., "Injectable Testosterone Undecanoate Has More Favourable Pharmacokinetics and Pharmacodynamics than Testosterone Enanthate," *European Journal of Endocrinology*, vol. 132, No. 4, pp. 514-519; 1995.
PCT/US01/10293 International Search Report (dated Feb. 26, 2002).
PCT/US02/09886 International Search Report (dated Aug. 6, 2002).
Rasmusson, Gary H. and Arth, Glen E., "Selective Synthesis of 14-Dehydroestranes," *Steroids*, 22, 107-111 (1973).
Segaloff, Albert and Gabbard, R. Bruce, "14-Dehydro-19-Nortestosterone and its 7α-methyl derivative," *Steroids* 22, 99-105 (1973).
Tauber et al., "Absolute Bioavailability of Testosterone After Oral Administration of Testosterone—Undecanoate and Testosterone," *European Journal of Drug Metabolism and Pharmacokinetics*, vol. 11, No. 2, pp. 145-150; 1986.
Zitzmann et al., "Hormone Substitution in Male Hypogonadism," *Molecular and Cellular Endocrinology*, vol. 161, No. 1-2, pp. 73-88; Mar. 30, 2000.

METHOD OF MAKING AND USING 7α, 11β-DIMETHYL-17β-HYDROXYESTR-4-EN-3-ONE 17-UNDECANOATE

CROSS-REFERENCE TO RELATED PATENT APPLICATIONS

This application is a continuation of co-pending U.S. patent application Ser. No. 12/184,600, filed Aug. 1, 2008, which is a continuation of U.S. patent application Ser. No. 11/040,964, filed Jan. 21, 2005, now abandoned, which in turn is a continuation of U.S. patent application Ser. No. 10/260,854, filed Sep. 30, 2002, now abandoned, which is a continuation of International Application No. PCT/US01/10293, filed Mar. 30, 2001, claiming the benefit of U.S. Provisional Patent Application Nos. 60/193,530, filed Mar. 31, 2000 and 60/194,440, filed Apr. 4, 2000. The disclosures of the '600 application, the '964 application, the '854 application, the '293 application, the '530 application and the '440 application are incorporated herein by reference.

FIELD OF THE INVENTION

The present invention generally relates to methods of making and using esters of androgenic steroids.

BACKGROUND OF THE INVENTION

Androgen is a term used to identify the human male sex hormones. These hormones, which are chemically classified as steroids, are produced in the body by the testis, the cortex of the adrenal gland and, to a much lesser extent, by the ovaries. Testosterone is perhaps the most widely recognized androgen, and is responsible for the development of male characteristics in a human, including secondary sexual characteristics, libido and the ability to produce sperm.

When a person is unable to synthesize testosterone, therapy directed at replacing the missing hormone is commonly undertaken. In practice, however, this therapy can be problematic. For example, testosterone exhibits only weak activity when administered orally. While parenteral administration is possible, it is impractical because testosterone remains active in the body for only a short time. Research has therefore focused on identifying so-called synthetic androgens that are acceptable substitutes for natural testosterone.

A number of oral and injectable synthetic androgens have been developed over the years, including esters of various androgens. While these esters are hydrolyzed in the body into their corresponding biologically-active alcohols, they are nonetheless administered because they slow the rapid degradation of the synthetic androgen by the body. This maximizes the amount of the biologically active alcohol that reaches the bloodstream.

Unfortunately, the activity of these androgen esters is unpredictable. Different androgens sharing the same ester group exhibit varying and unpredictable levels of activity, as do androgens having the same basic chemical structure, but different ester groups.

One of the esters that has emerged as a viable injectable synthetic androgen is testosterone enanthate. This enanthate is presently used extensively via intramuscular (IM) injection for hormone replacement therapy in hypogonadal men, and as the androgenic component of several experimental male contraceptives. One drawback of this active is that it is not exceptionally long-acting—it must be administered IM every two weeks to maintain testosterone levels within a normal (therapeutic) range in hypogonadal men.

More specifically, testosterone enanthate is presently administered IM for the treatment of hypogonadism at a dose of 200 mg every two or three weeks. If this enanthate is used for male contraception, it may be administered parenterally at from about 200-400 mg every week, and if used as the androgenic component with estrogen or progestins for contraception, it may be administered at about 200 mg every two weeks. Testosterone bucyclate is another synthetic androgen disclosed in, e.g., U.S. Pat. No. 4,948,790. If administered parenterally for the treatment of hypogonadism, this bucyclate would require a dose of about 1200 mg (given as 3 injections of 1 ml each due to its solubility) to retain activity for about 2-3 months.

The development of androgens that exhibit activity after oral administration has been less successful. At present, the most widely used effective oral formulation includes methyltestosterone as the active ingredient, administered at 10-50 mg methyltestosterone/day. However, this active cannot be administered on a long-term basis, as is required in androgen replacement therapy, because of its associated liver toxicity. It is well known that androgens alkylated at the $C_{17}$ position, such as methyltestosterone, exhibit such toxicity. While removal of the $C_{17}$ alkyl group may appear at first glance to be an obvious solution to this problem, alkylation at this position is believed to be necessary to prevent degradation of the active by the liver after oral administration.

Illustrative of the development efforts relating to synthetic androgens is U.S. Pat. No. 5,952,319. While this patent identifies a number of potentially-active synthetic androgens, including 7α,11β-dimethyl-17β-hydroxy-4-estren-3-one 17β-trans-4-n-butylcyclohexane carboxylate (referred to herein as 7α,11β-dimethyl-17β-hydroxy-4-estren-3-one bucyclate), it provides no data regarding the biological activity of 7α,11β-dimethyl-17β-hydroxy-4-estren-3-one bucyclate. There is similarly no data available concerning the biological activity of another synthetic androgen, 7α,11β-dimethyl-17β-hydroxyestr-4-en-3-one 17-undecanoate.

A need therefore exists for a means of overcoming the foregoing and other problems associated with androgen replacement and other therapies that require the administration of androgens.

BRIEF SUMMARY OF THE INVENTION

The present invention meets the aforesaid and other needs by providing, in one aspect, a method for providing hormonal therapy to a patient comprising the oral administration of about 1 mg/day to about 25 mg/day of 7α,11β-dimethyl-17β-hydroxy-4-estren-3-one bucyclate, 7α,11β-dimethyl-17β-hydroxyestr-4-en-3-one 17-undecanoate, or a mixture thereof, to a patient in need thereof.

This aspect of the invention is predicated in significant part on the unexpected discoveries that 7α,11β-dimethyl-17β-hydroxy-4-estren-3-one bucyclate (also referred to herein as "the bucyclate") and 7α,11β-dimethyl-17β-hydroxyestr-4-en-3-one 17-undecanoate (also referred to herein as "the undecanoate") do not degrade after oral administration even though each lacks an alkyl group at the $C_{17}$ position, and exhibit activity far in excess of the current oral standard, methyltestosterone. These surprising discoveries permit hormonal therapies requiring the administration of an androgen to be conducted utilizing oral dosages of the bucyclate and/or the undecanoate that are significantly lower than those required when administering oral methyltestosterone to effect the same therapy. A further expected benefit of using the bucyclate and undecanoate is that liver toxicity, if any, should be minimal because these compounds are not alkylated at the $C_{17}$ position.

In another aspect, the present invention comprises a method for providing hormonal treatment comprising the parenteral administration of from about 1 mg up to about 100 mg of the bucyclate and/or the undecanoate at intervals of at least about two weeks, and preferably up to about 600 mg at much longer intervals, e.g., a single administration of 600 mg providing effective therapy for up to about three months.

This aspect of the invention is predicated in part on the surprising relatively high potency, and unexpected long-term activity, of the bucyclate and undecanoate when administered parenterally, which potency is higher and activity longer-lasting than esters of other potent androgenic steroids, even bucyclic esters thereof. This activity was unexpected in view of the preparation and evaluation of several bucyclic esters of potent androgenic steroids other than 7α,11β-dimethyl-17β-hydroxy-4-estren-3-one bucyclate, the former group of esters yielding disappointing results.

Another aspect of the present invention includes separate processes for preparing the bucyclate and undecanoate, which provide these actives in relatively high yield, and advantageously in a solid form, preferably crystalline, at room temperature. As both can be produced in solid form, the preparation of aqueous microcrystalline suspensions for parenteral administration is possible. Moreover, because these actives are solid at room temperature, one is able to control the average particle size and particle size distribution of the solids, thereby positively affecting the duration of activity after parenteral administration of the respective suspensions.

Related aspects of the present invention include certain intermediates, in amorphous or, preferably, crystalline form, as well as one or more steps used in the aforementioned preferred process for preparing the bucyclate and the undecanoate.

Further aspects of the present invention include various formulations of these two actives, including tablets, caplets, extended release tablets, soft gelcaps containing the bucyclate and/or undecanoate in an oily carrier, transdermal patches, pre-filled syringes, vials and the like, in which the amount of the bucyclate and/or undecanoate included therein may be determined in view of their unexpected relatively high potency and long-term activity.

It is contemplated that the hormonal therapy of the present invention includes, but is not limited to, hormone replacement therapy in males and females, male contraception, and the treatment of certain cancers, such as breast cancer in females.

These and other aspects and features of the present invention may best be understood with reference to the accompanying figures and in the following description of the preferred embodiments.

BRIEF DESCRIPTION OF THE DRAWINGS

FIG. 6 depicts the androgenic activity of CDB-4386A following subcutaneous or oral administration (CDB-110, methyltestosterone, oral standard; CDB-111C, testosterone, subcu standard) "Hershberger Test," ● CDB-4386A oral; ○ CDB-4386A subcutaneous; ▲ CDB-110 oral standard; -▽- CDB-111C subcutaneous standard; — Fitted line; - - - Vehicle control oral and subcutaneous; and

|  | ANDROGENIC ACTIVITY | |
|---|---|---|
| ROUTE | Potency Ratio | 95% C.I. |
| Oral | 3.77[a] | 2.25-6.33 |
| Subcutaneous | 0.39[b] | 0.24-0.63 |

[a]Methyltestosterone oral standard = 1.0 (assigned);
[b]Testosterone subcutaneous standard = 1.0 (assigned).

Figure 7:
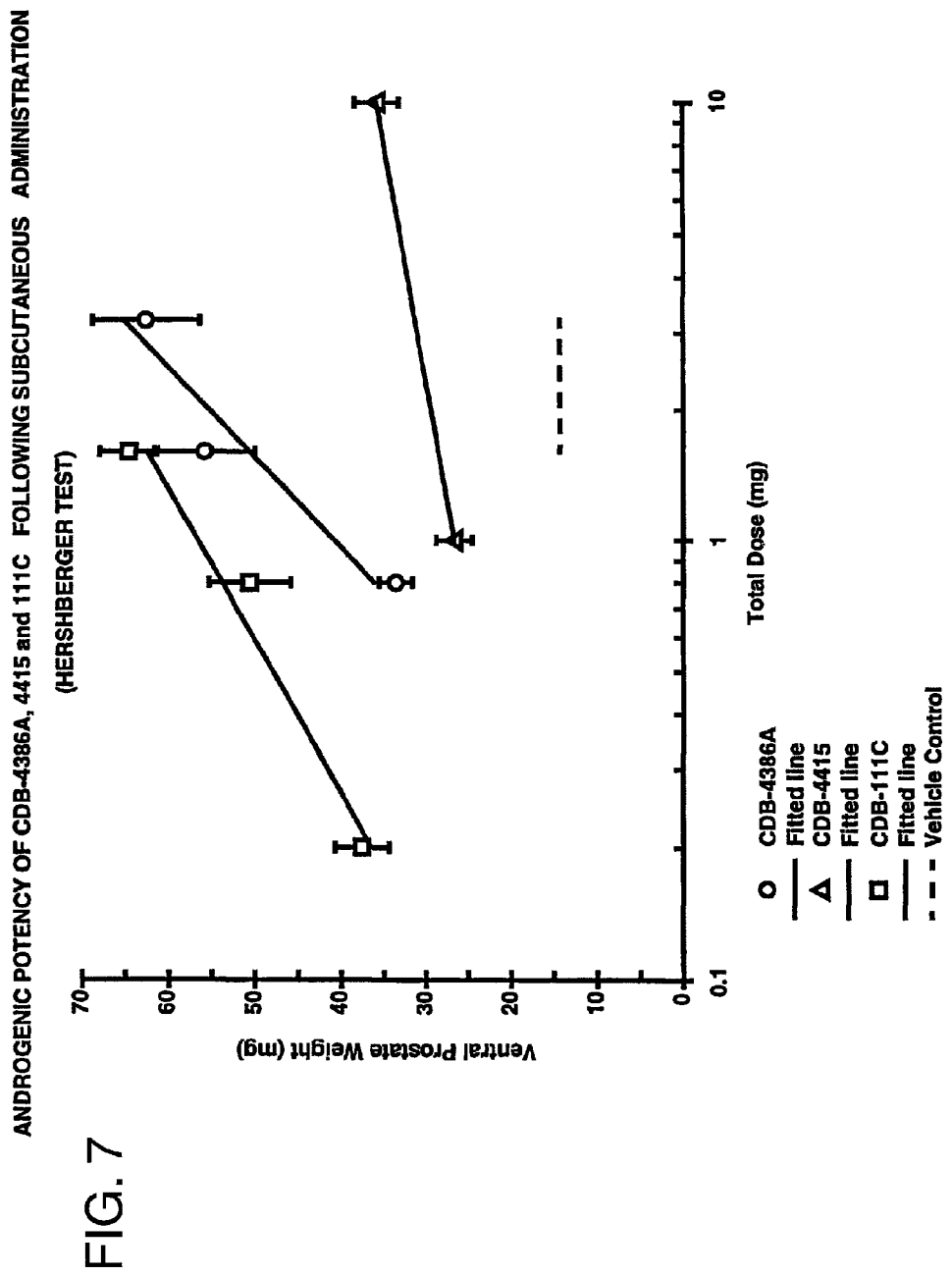

FIG. 7 is a graph comparing the androgenic potency of 7α,11β-dimethyl-17β-hydroxy-4-estren-3-one bucyclate and that of other compounds after subcutaneous injection.

Figure 8:
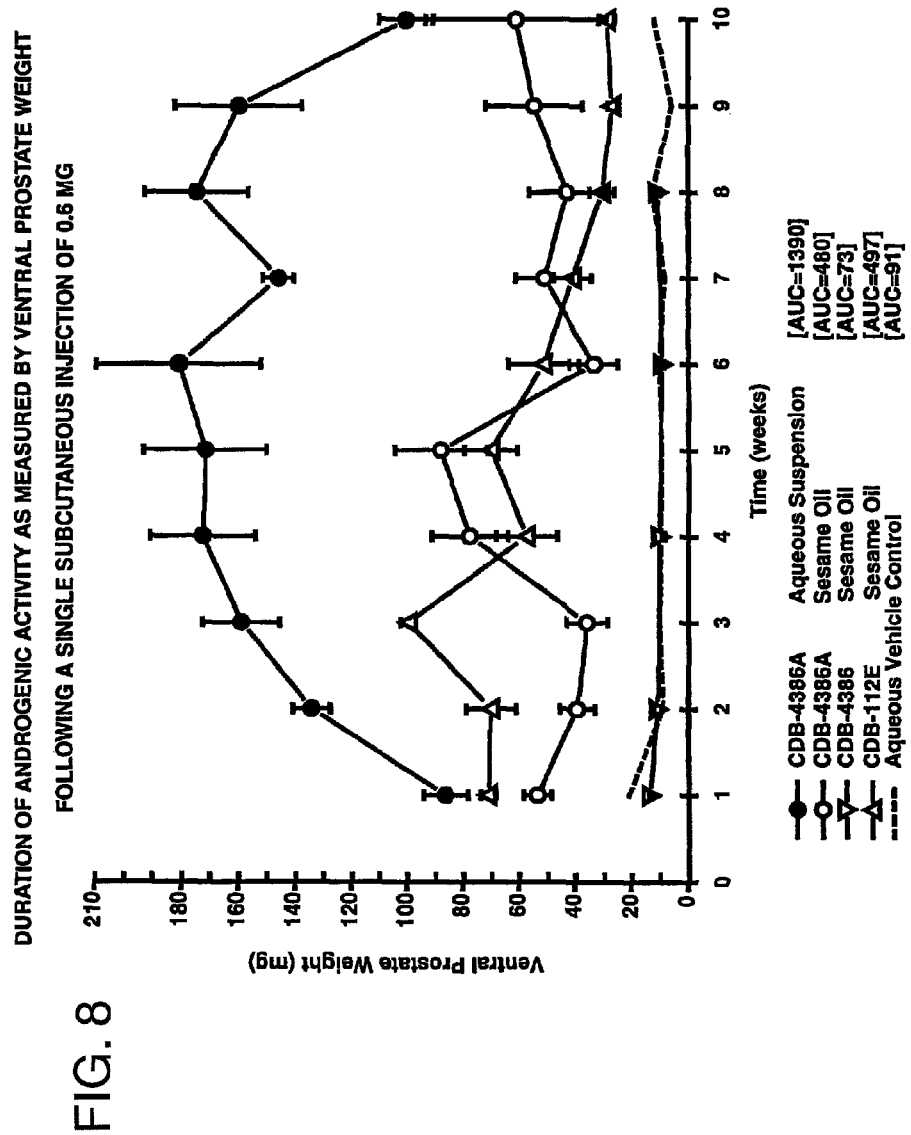

FIG. 8 is a graph comparing the duration of activity of 7α,11β-dimethyl-17β-hydroxy-4-estren-3-one bucyclate and that of other compounds after subcutaneous injection.

Figure 9:
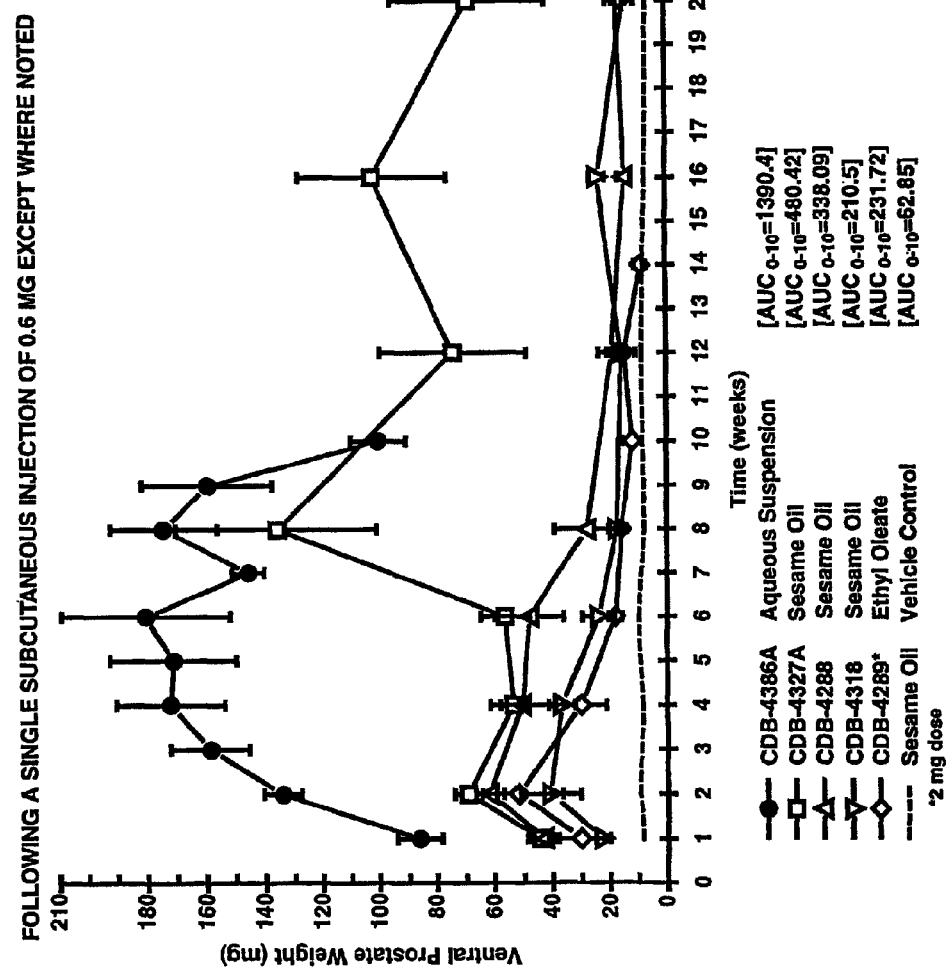

FIG. 9 is a graph comparing the duration of activity of 7α,11β-dimethyl-17β-hydroxy-4-estren-3-one bucyclate and that of other compounds after subcutaneous injection.

Figure 10:
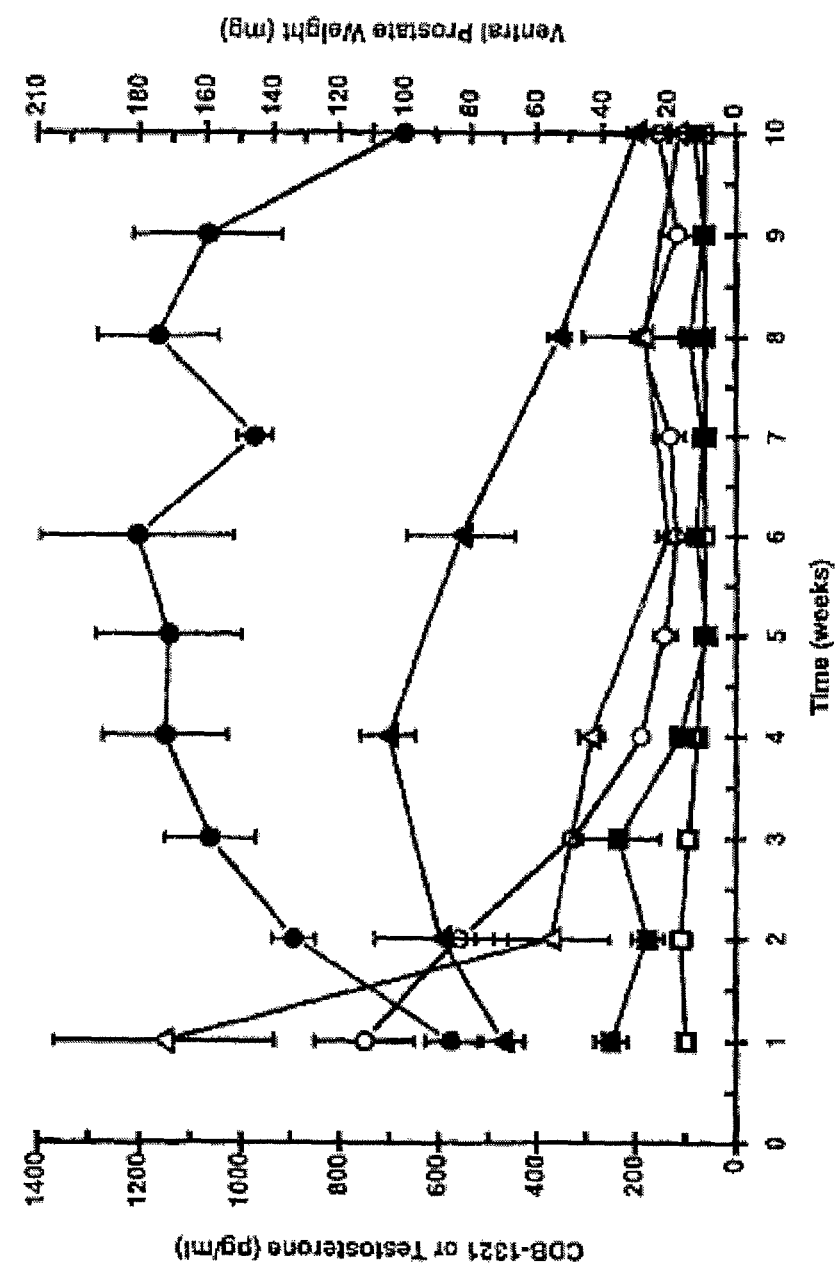

FIG. 10 is a graph comparing testosterone serum levels (pg/ml) after subcutaneous injection of 7α,11β-dimethyl-17β-hydroxy-4-estren-3-one bucyclate and other compounds. The Y-axis depicts ventral prostate weight and serum levels of CDB-1321 or testosterone in castrate Sprague-Dawley rats following a single subcutaneous injection of CDB-4386A, 1321 or 1781a in aqueous suspending vehicle at the dose levels indicated (n=5), -○- CDB-4386A (0.6 mg) 1321 pg/ml; (R) -●- CDB-4386A (0.6 mg) V.P. Wt.; -□- CDB-1321D (0.6 mg) 1321 pg/ml; (R) -■- CDB-1321D (0.6 mg) V.P. Wt.; -△- CDB-1781a (1.0 mg) T pg/ml; and (R) -▲- CDB-1781a (1.0 mg) V.P. Wt.

Figure 11:
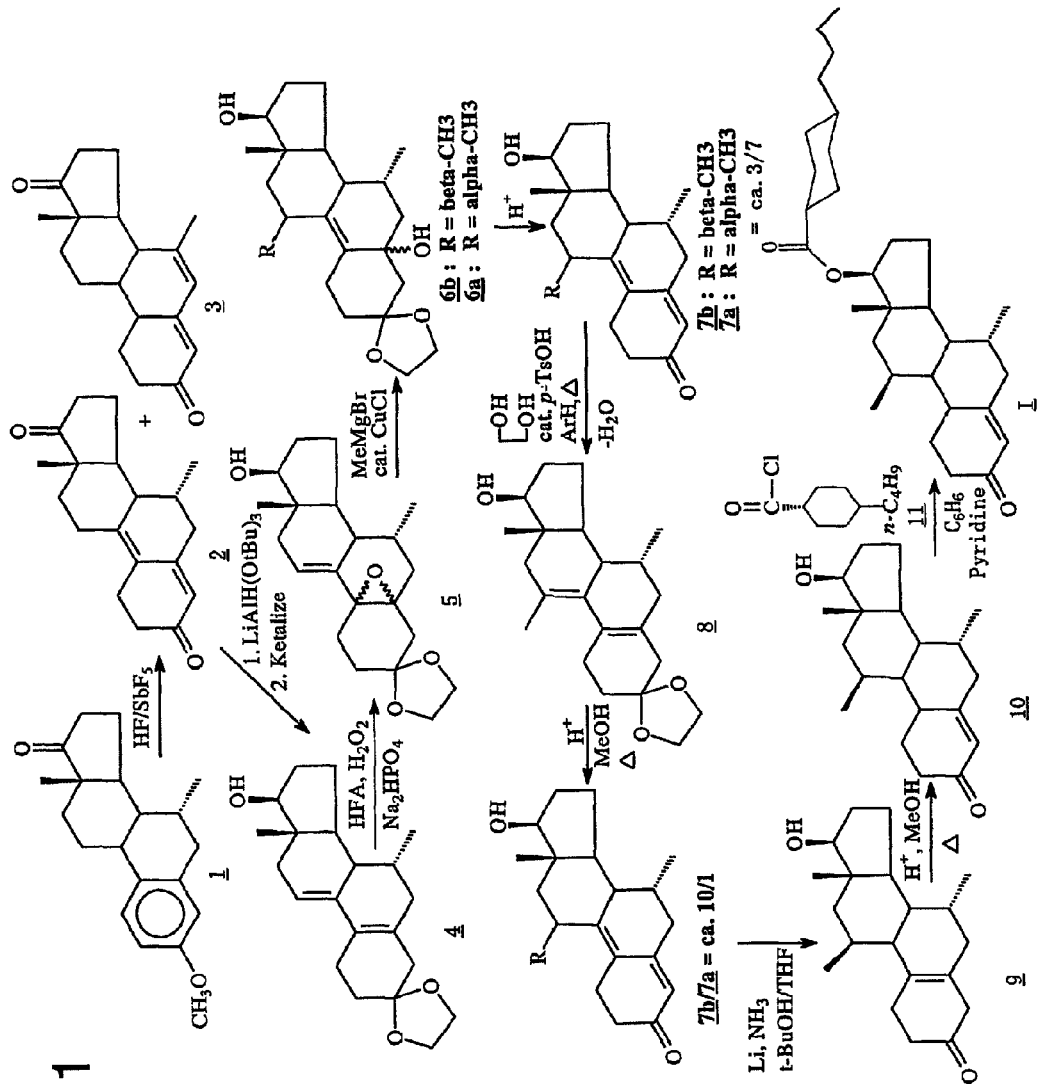

FIG. 11 is a description of a preferred method for preparing 7α,11β-dimethyl-17β-hydroxy-4-estren-3-one bucyclate.

Figure 12:
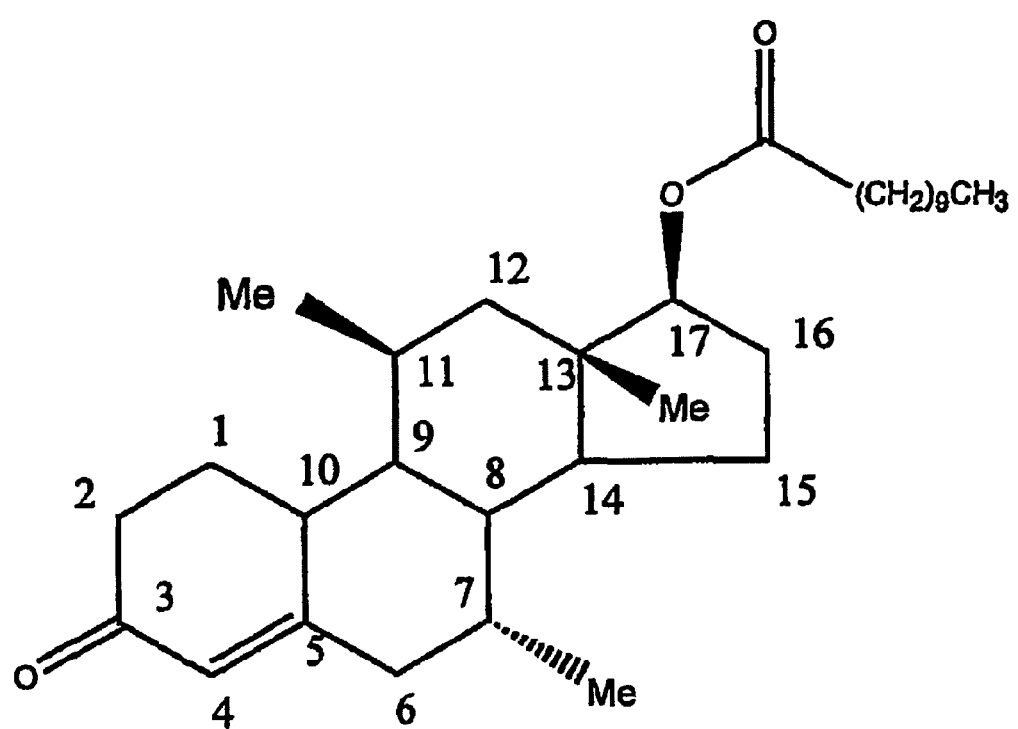

FIG. 12 illustrates the chemical structure of 7α,11β-dimethyl-17β-hydroxyestr-4-en-3-one 17-undecanoate, with numerals identifying the various carbon atom positions, including the non-alkylated $C_{17}$ position.

Figure 13:
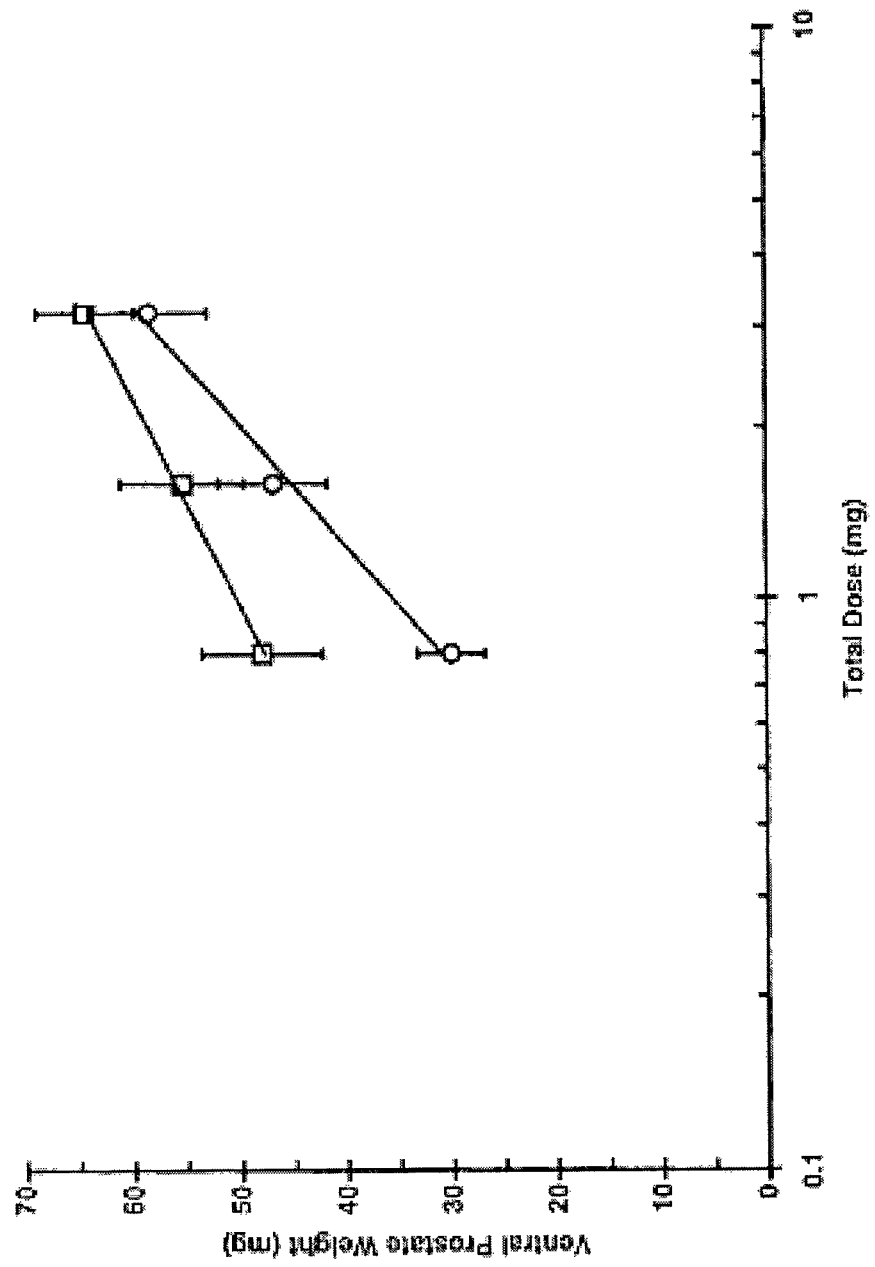

FIG. 13 is a graph comparing the androgenic potency of 7α,11β-dimethyl-17β-hydroxyestr-4-en-3-one 17-undecanoate and testosterone after subcutaneous injection. FIG. 13 depicts the androgenic activity of CDB-4521A and CDB-111C (testosterone) in castrate Sprague-Dawley rats following subcutaneous administration in 10% EtOH/sesame oil (Hershberger Test—ventral prostate weight), ○ CDB-4521A; □ CDB-111C; — Fitted line; - - - - Vehicle control; and

| CDB NO. | ANDROGENIC ACTIVITY | |
|---|---|---|
| | Potency Ratio | 95% C.I. |
| 111C | 1.00 (assigned) | — |
| 4521 | 0.52 | 0.29-0.93. |

Figure 14:
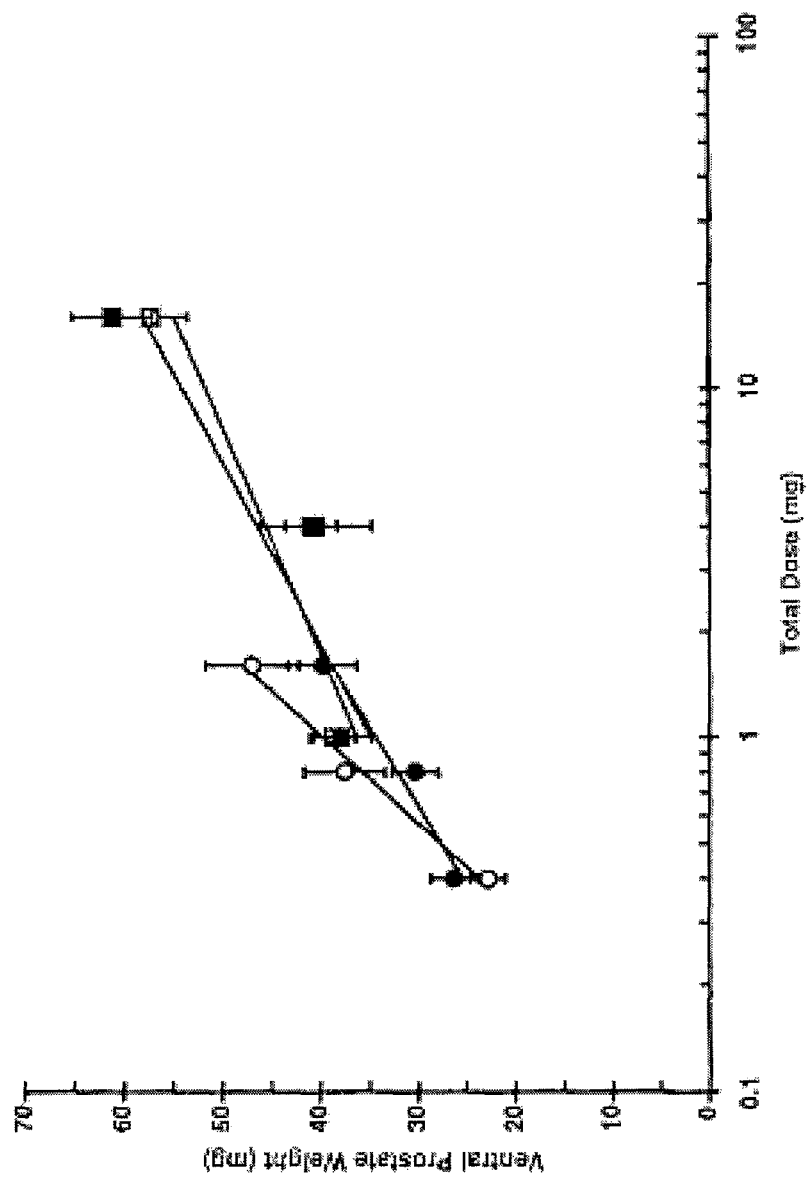

FIG. 14 is a graph comparing the androgenic potency of 7α,11β-dimethyl-17β-hydroxyestr-4-en-3-one 17-undecanoate and methyltestosterone after oral administration. FIG. 14 depicts androgenic activity of CDB-4521A and CDB-110 (methyltestosterone) following oral administration in 10% EtOH/sesame oil or aqueous suspending vehicle "Hershberger Test," ○ CDB-4521A 10% EtOH/Sesame Oil; ● CDB-4521A (Aqueous Suspending Vehicle); □ CDB-110 10% EtOH/Sesame Oil; ■ CDB-110 Aqueous Suspending Vehicle; — Fitted line; - - - Vehicle Control (Aqueous Suspending Vehicle); and

| VEHICLE | ANDROGENIC ACTIVITY | |
|---|---|---|
| | Potency Ratio[a] | 95% C.I. |
| EtOH/SO | 2.36[b] | — |
| ASV | 0.95 | 0.36-2.5 |

[a]Methyltestosterone oral standard = 1.0 (assigned);
[b]Did not pass significance tests.

Figure 15:
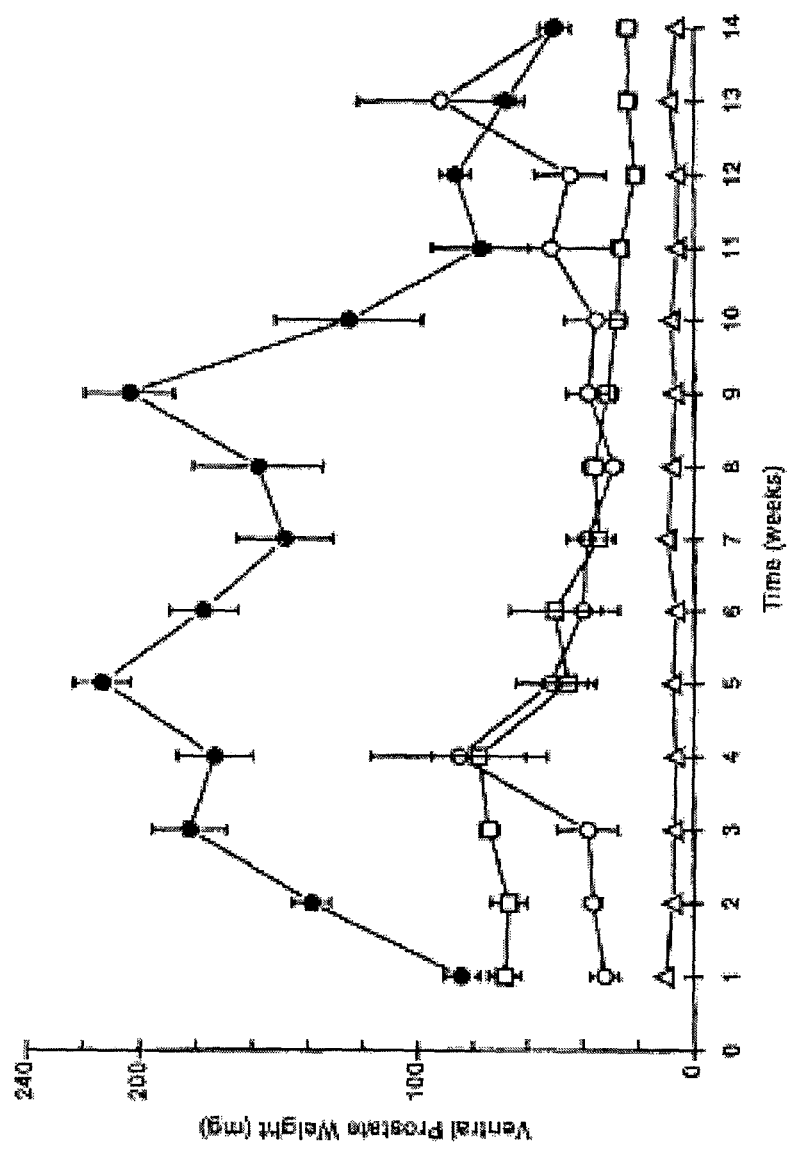

FIG. 15 is a graph comparing the duration of activity of 7α,11β-dimethyl-17β-hydroxyestr-4-en-3-one 17-undecanoate and that of testosterone enanthate (CDB-112F) after subcutaneous injection. The Y-axis depicts -○- CDB-4521 10% EtOH/Sesame Oil [AUC=620]; -□- CDB-112F 10% EtOH/Sesame Oil [AUC=559.28]; -Δ- Vehicle Control (10% EtOH/Sesame Oil) [AUC=95]; and -●- CDB-4521 Aqueous Suspending Vehicle [AUC=1817].

Figure 16:
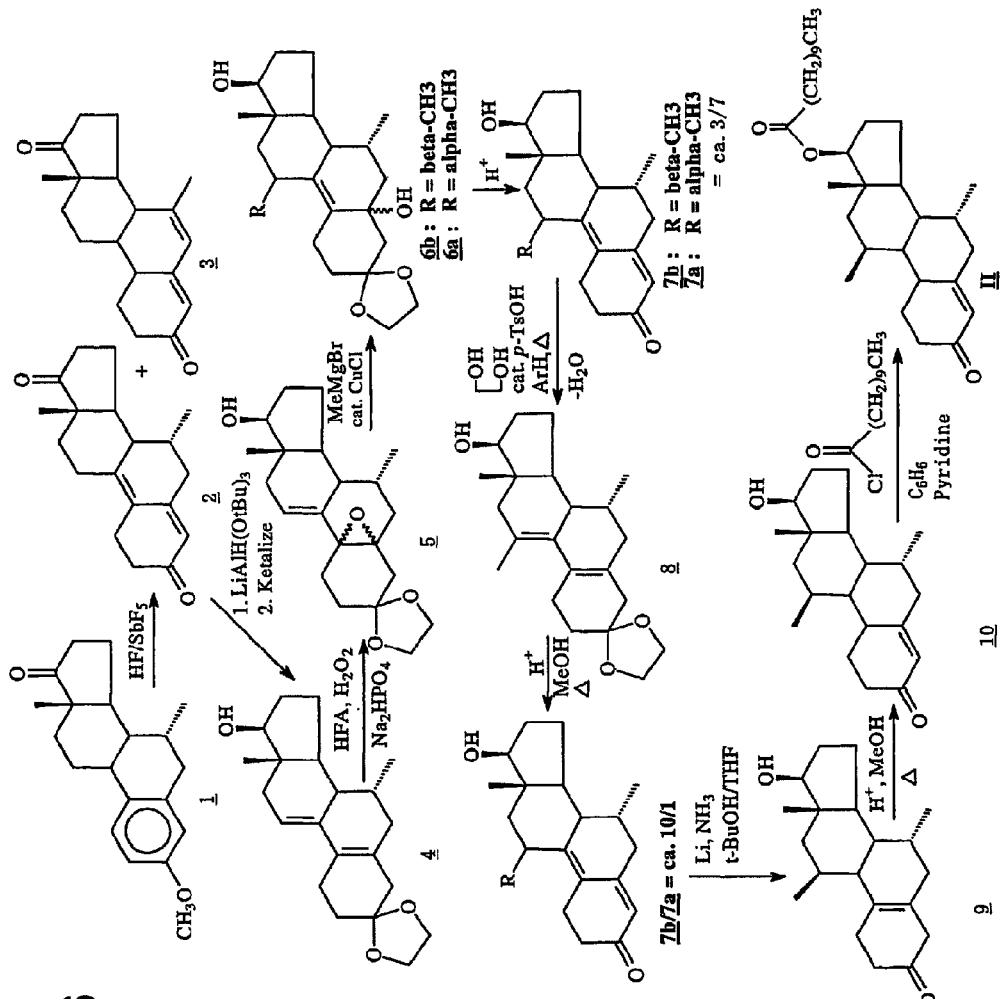

FIG. 16 is a description of a preferred method for preparing 7α,11β-dimethyl-17β-hydroxyestr-4-en-3-one 17-undecanoate.

The various aspects of the present invention described in the following paragraphs are set forth with an emphasis on preferred embodiments. However, it will be obvious to those of ordinary skill in the art that variations of the preferred embodiments may be successfully used, and that it is intended that the invention may be practiced otherwise than as specifically described herein. The inventive methods, processes and formulations should therefore not be construed as being limited to the preferred embodiments described herein.

DETAILED DESCRIPTION OF THE PREFERRED EMBODIMENTS

Figure 1:
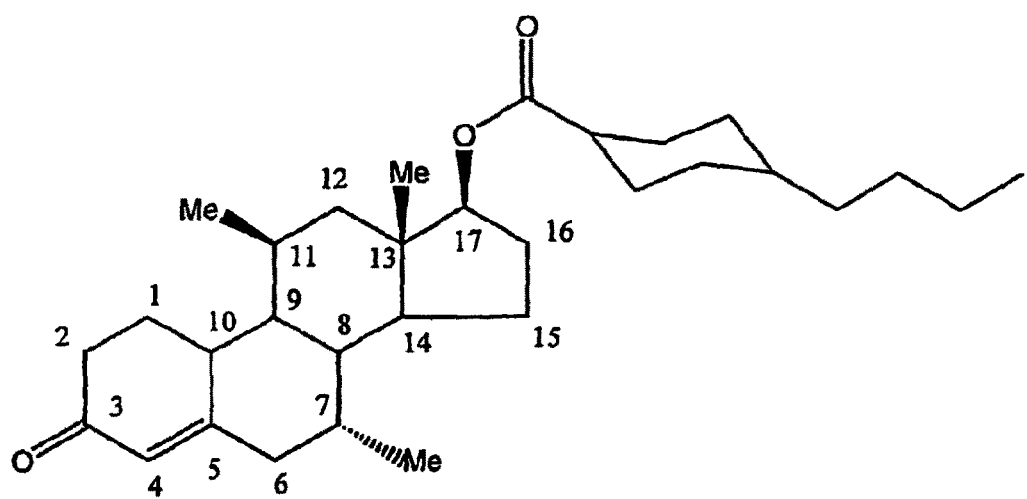
FIG. 1 illustrates the chemical structure of 7α,11β-dimethyl-17β-hydroxy-4-estren-3-one bucyclate, with numerals identifying the various carbon atom positions, including the non-alkylated $C_{17}$ position.

The present invention provides a variety of methods for providing hormonal therapy to a patient in need thereof. Each method requires the administration of particular actives, 7α,11β-dimethyl-17β-hydroxy-4-estren-3-one bucyclate, and 7α,11β-dimethyl-17β-hydroxyestr-4-en-3-one 17-undecanoate, either in combination or, preferably, alone. The chemical structure of the bucyclate and undecanoate actives, with numerals identifying the various carbon atom positions, are set forth in FIGS. 1 and 12, respectively.

Figure 2A:
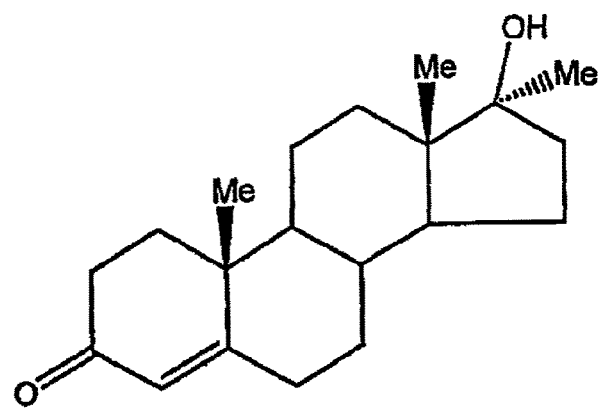
FIG. 2A illustrates the chemical structure of methyltestosterone.
Figure 2B:
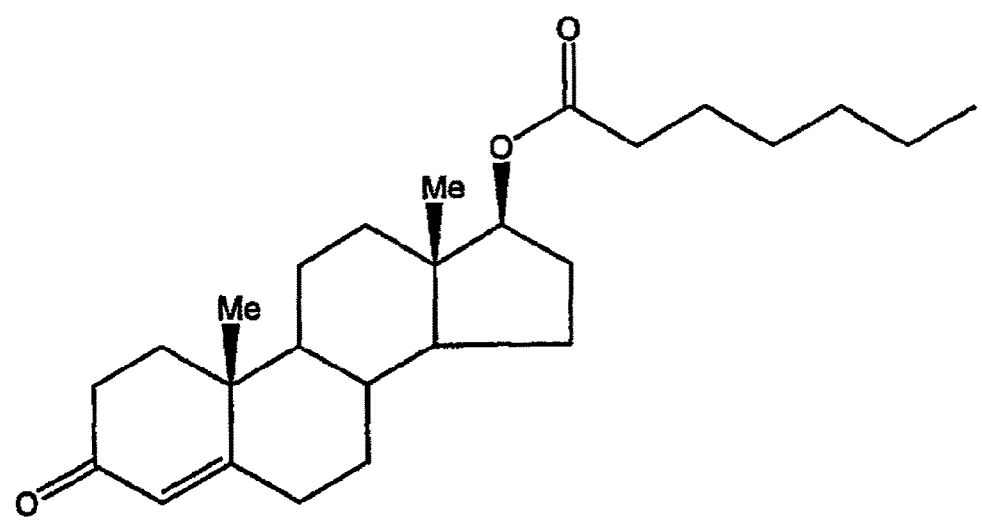
FIG. 2B illustrates the chemical structure of testosterone enanthate.

In significant part, the present invention rests upon the discovery that both 7α,11β-dimethyl-17β-hydroxy-4-estren-3-one bucyclate and 7α,11β-dimethyl-17β-hydroxyestr-4-en-3-one 17-undecanoate exhibit surprising and unexpected properties in vivo. These properties permit these actives to be administered either orally or parenterally, in relatively lower amounts, at longer time intervals, and with less side effects, as compared to existing alternative synthetic androgens, e.g., methyltestosterone, testosterone enanthate. The chemical structures of these two well-known compounds (methyltestosterone, testosterone enanthate) are set forth in FIGS. 2A and 2B, respectively.

The surprising properties of 7α,11β-dimethyl-17β-hydroxy-4-estren-3-one bucyclate and 7α,11β-dimethyl-17β-hydroxyestr-4-en-3-one 17-undecanoate render these actives well suited for any hormonal therapy in which an androgen is required, or desired. By way of example only, and without intending to limit the therapeutic uses of the actives, the actives may be used in the treatment of hypogonadal males. The actives may also be administered (either alone or, more effectively, in combination with one or more steroidal progestins or estrogens) to induce and maintain fertility suppression in male animals. Further, and due to their anabolic properties, the actives may be administered to promote and maintain muscle growth and maintenance. These properties can be particularly important in persons afflicted with muscle wasting diseases such as AIDS, but are more generally applicable to the elderly who typically have relatively low muscle mass. In addition, the actives may be used for the treatment of cancer, e.g., the pilliative treatment of breast cancer in women.

The unexpected properties of 7α,11β-dimethyl-17β-hydroxy-4-estren-3-one bucyclate and 7α,11β-dimethyl-17β-hydroxyestr-4-en-3-one 17-undecanoate were discovered after a series of in vivo animal studies undertaken in Sprague-Dawley rats. Based upon these experiments, it was unexpectedly found that the bucyclate and undecanoate, despite their lack of alkylation at the $C_{17}$ position, not only do not degrade after oral administration, but exhibit activity far in excess of the current oral standard, methyltestosterone. Moreover, this lack of alkylation is expected to minimize, or eliminate, any attendant liver toxicity. Thus, the foregoing and other therapies may be conducted utilizing dosages of the bucyclate and undecanoate that are significantly lower than those expected, and less than that required when administering methyltestosterone, to effect the same therapy. This is accomplished without the attendant concern of liver toxicity associated with existing synthetic androgens.

More specifically, it was found that the oral activity of 7α,11β-dimethyl-17β-hydroxy-4-estren-3-one bucyclate was about four times greater than methyltestosterone. The oral activity of the undecanoate, 7α,11β-dimethyl-17β-hydroxyestr-4-en-3-one 17-undecanoate, was found to be about twice that of methyltestosterone. Moreover, and with respect to both the bucyclate and undecanoate, it was found that this oral activity was maximized when the actives were formulated with an oily carrier. Unexpectedly high levels of activity were also discovered in connection with the parenteral administration of the bucyclate and undecanoate. In contrast to the oral formulation, activity was maximized when the parenteral formulation comprised the actives in an aqueous carrier.

As a general statement, it was found that the effective oral dosage of 7α,11β-dimethyl-17β-hydroxy-4-estren-3-one bucyclate for any hormone replacement therapy which requires an androgen, e.g., the treatment of hypogonadism, will be about one-fourth the oral dosage of methyltestosterone required to provide the same effect. For example, and in the case of hypogonadism, 7α,11β-dimethyl-17β-hydroxy-4-estren-3-one bucyclate may be orally administered in therapeutically effective amounts. More specifically, the oral dosage may range from about 1 mg/day to about 25 mg/day, advantageously from about 2 mg/day to about 20 mg/day, and preferably up to about 15 mg/day. Administration of the undecanoate to effect this therapy may be undertaken within the foregoing bucyclate therapeutic dosage ranges, but is preferably undertaken at relatively greater levels relative to that of the bucyclate due to the undecanoate's slightly lower oral activity. For example, the undecanoate may be administered at from about 1 mg/day to about 75 mg/day, advantageously from about 2 mg/day to about 50 mg/day, and preferably up to about 25 mg/day.

The oral dosage regimens described herein, set forth on the basis of milligrams/day, includes any dosage regiment is able to provide that dosage level to a patient per day. For example, an extended release formulation of the bucyclate or undecanoate would not need to be administered each day, yet would provide the required daily dosage. However, administration of the therapeutic dosage on a daily basis the preferred method of treatment.

The effective oral dosage of bucyclate for the treatment of cancer, e.g., breast cancer in women can vary, but will range from at least about 10 mg/day, advantageously at least about 25 mg/day, and preferably at least about 50 mg/day. Administration of the undecanoate to effect this therapy may, as before, be undertaken within the foregoing bucyclate therapeutic dosage ranges, but is preferably undertaken at relatively greater levels relative to that of the bucyclate. For example, the undecanoate may be administered in an amount of at least about 20 mg/day, advantageously at least about 50 mg/day, and preferably at least about 100 mg/day.

In the use of 7α,11β-dimethyl-17β-hydroxy-4-estren-3-one bucyclate for male contraception, an effective oral dose may range from about 1 mg/day to about 25 mg/day, advantageously from about 2 mg/day to about 20 mg/day, and up to about 15 mg/day. Administration of the undecanoate to effect this therapy may, as before, be undertaken within the foregoing bucyclate therapeutic dosage ranges, but is preferably undertaken at relatively greater levels relative to that of the bucyclate. For example, the undecanoate may be administered in an amount ranging from about 1 mg/day to about 50 mg/day, advantageously from about 2 mg/day to about 40 mg/day, and up to about 30 mg/day.

In the case of conditions requiring chronic hormonal therapy, such as hypogonadism, an injectable bucyclate and/or undecanoate formulation is preferably administered. This preference is based upon the unexpected discovery that these actives are surprisingly potent and long-acting when dispersed (preferably as a suspension) in an aqueous formulation. Given these properties, the bucylate and undecanoate may be administered in an aqueous formulation at lower doses compared to both testosterone enanthate (in an oily carrier) and testosterone bucyclate, and at relatively long intervals. More specifically, and by way of comparative example, doses of the bucyclate and undecanoate, when dispersed in an aqueous formulation, may generally range from about one-third to about three-quarters the dose of testosterone enanthate (provided in a sesame oil carrier) required to provide substantially equivalent therapeutic results, with between about one-half and about two-thirds of that latter dose being preferred. With respect to testosterone enanthate, the bucyclate and undecanoate, when dispersed in an aqueous carrier, may be administered at between about one-quarter and about one-half of the dose of testosterone enanthate to provide substantially equivalent therapeutic effects. However, if either active is formulated in a non-aqueous carrier, e.g., an oily carrier comprised of sesame or other vegetable oils, it was discovered that its potency over long periods remained, but that it was substantially equivalent to that of testosterone enanthate in a sesame oil carrier.

Because of its long-acting androgenic activity, particularly when administered parenterally in an aqueous carrier in effective amounts, the bucyclate and undecanoate may be administered at intervals equal to, or in excess of, about two weeks. More specifically, they may be administered at intervals of about one month, preferably about two months, and most preferably once about every three months. This provides a significant advantage to a patient relative to existing regimens which require therapeutic injections on a more frequent basis.

Again, the dosage of either the bucyclate or undecanoate administered parenterally in an aqueous formulation at any intervals will be significantly less than the amount of testosterone enanthate used to achieve substantially similar therapeutic results. For example, in treating hypogonadism, the bucyclate and undecanoate may be administered in amounts ranging from about 1 mg up to about 100 mg about every two weeks, and advantageously from about 25 to about 75 mg during that period; up to about 200 mg about every month, and advantageously from about 50 mg to about 150 mg during that time period; up to about 400 mg about every 2 months, and advantageously from about 100 to about 300 mg during that time period; and up to about 600 mg about every 3 months, and advantageously from about 150 mg to about 450 mg during that time period. These dosages, advantageously provided by a single injection at the beginning of each time period, are less than the dosages of testosterone enanthate and testosterone bucyclate that may be used to provide similar therapeutic effects over the same periods.

By way of further example, dosages of the bucyclate or undecanoate effective for male contraception via parenteral administration, if used alone, may range from about 25 mg/week up to about 200 mg/week, advantageously up to about 150 mg/week, and preferably from about 50 mg/week to about 100 mg/week. If used in a more typical manner, i.e., combined with estrogen and/or progestins, parenteral dosages of the bucyclate or undecanoate may range from about 1 mg up to about 100 mg every about two weeks, advantageously from about 2 mg up to about 75 mg, and preferably up to about 50 mg, every two weeks. Of course, because of the long-acting activity of the bucyclate and undecanoate, these dosages may be administered on a substantially linear basis if activity beyond the periods set forth above.

The enhanced potency of the bucyclate and undecanoate advantageously permits a further advantage in that effective amounts may be administered via a single injection, which is desirable from a patient comfort and cost perspective.

Equivalent therapeutic results using testosterone enanthate would require multiple injections. Of course, multiple injections of relatively lower doses of the bucyclate or undecanoate may be administered if required or desired.

While the bucyclate or undecanoate may be administered alone in the treatment of cancer, it is preferably administered in coordination with one or more anti-cancer agents, e.g., therapeutically-effective amounts of chemotherapeutic agents, such as, cisplatin, carboplatin, doxorubicin, paclitaxel, taxotere, methotrexate, fluorouracil, camptothecin, cyclophosphamide and mixtures thereof, as well as therapeutically-effective amounts of anti-angiogenesis agents, either alone or in combination. The identity of suitable anti-tumor and anti-angiogenesis agents and associated dosage regimens are well known, and as such will not be repeated herein. The timing of administration of the foregoing agents may occur at any time so long as the administration does not interfere with the inventive therapeutic methods.

While the bucyclate and undecanoate may be prepared using any suitable process, a further aspect of the present invention is the discovery of the preferred synthesis routes described below, which provide these actives in relatively high yield, and in solid form, preferably in crystalline form, at room temperature. The preparation of these actives in solid form at room temperature was significant, as it led to the further discovery that the long-acting effect of these actives are enhanced when included in an injectable formulation at an average particle diameter of from about 1-50 and preferably from about 3-30 μm. The average particle diameter of the bucyclate or undecanoate when formulated as an injectable is thus preferably within the foregoing ranges.

As a solid at room temperature, the bucyclate and undecanoate stand in marked contrast to testosterone enanthate. The latter exists as a liquid at room temperature, adversely affecting its activity over long periods of time. Further, the enanthate is precluded from commercialization as a lyophilizate or powder for reconstitution, or as a tablet, caplet or other solid dosage form.

Turning to FIG. 11, the preferred synthesis of 7α,11β-dimethyl-17β-hydroxy-4-estren-3-one bucyclate is depicted. Generally, this synthesis comprises the steps of:

(a) converting the ether group of Compound 1

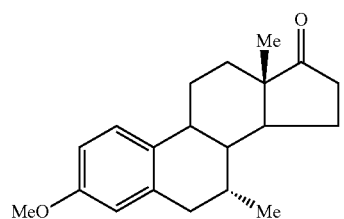

to a carbonyl group, providing Compound 2

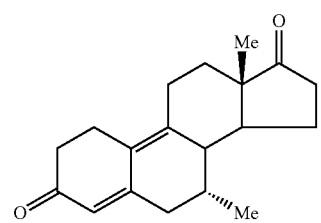

(b) ketalizing the carbonyl group of Compound 2 to provide Compound 4

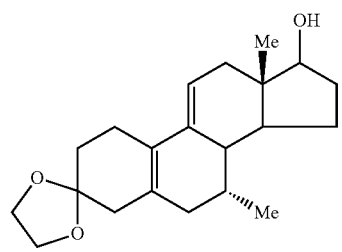

(c) epoxidizing Compound 4 to provide the epoxide of Compound 5

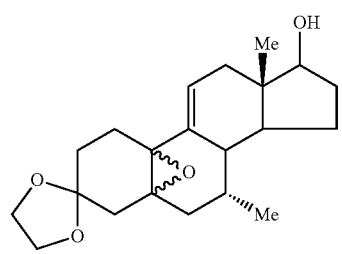

(d) opening the epoxide ring in Compound 5 and substituting an alkyl group at $C_{11}$ to provide Compound 6 (comprising a mixture of 11α- and 11β-methyl isomers, Compounds 6a and 6b, respectively) by use of a Grignard reagent

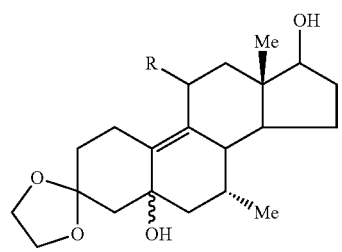

6a: R = alpha-Me
6b: R = beta-Me (e) deketalizing and dehydrating Compound 6 to provide Compound 7 (comprising a mixture of 11α- and 11β-methyl isomers, Compounds 7a and 7b, respectively)

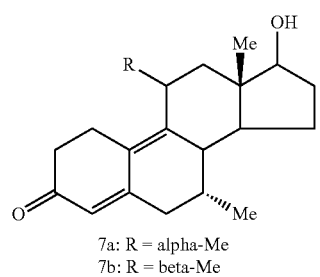

7a: R = alpha-Me
7b: R = beta-Me (f) converting Compound 7a to Compound 9

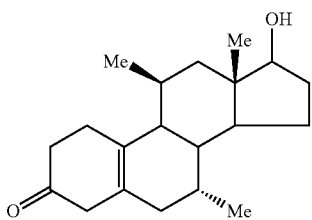

9

(g) converting Compound 9 to Compound 10

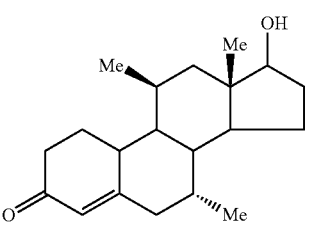

10 and (h) esterifying Compound 10 to provide Compound I (7α,11β-dimethyl-17β-hydroxy-4-estren-3-one bucyclate).

Step (a) may also yield an undesirable by-product, Compound 3

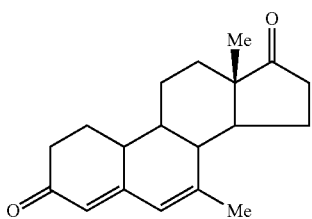

3

If desired, before step (f), one may ketalize the 11α- and 11β-methyl isomers of Compound 7 to provide Compound 8

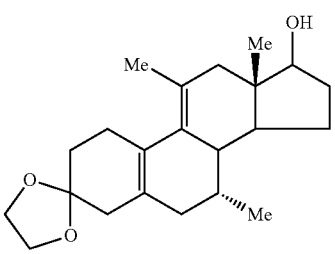

8 and then deketalize and epimerize Compound 8, thereby enhancing the ratio of the desirable 11α-methyl isomer to 11β-methyl isomer.

Turning to FIG. 16, a preferred synthesis route for the preparation of the undecanoate is set forth. This synthesis comprises steps (a)-(g) used in the bucyclate synthesis as set forth above. Thereafter, however, Compound 10 is esterified to provide Compound II (the undecanoate).

One or more of the intermediates formed during the foregoing synthesis routes are also contemplated as part of the present invention, and particularly the preferred crystalline forms of those intermediates. In addition, certain of the process steps, and combinations thereof, which provide advantages such as relatively high yields and/or purities of intermediates, constitute further aspects of the present invention.

A pharmaceutically acceptable carrier is advantageously combined with each active to ease the administration of the active to a patient in need. Suitable carriers for oral and buccal dosage forms, such as tablets, capsules, caplets and soft gelcaps (having an oily carrier), are well known, and may be used in connection with the actives. Preferably, oral dosage formulations of the bucyclate and/or undecanoate include an oily carrier, and are provided in the form of a soft gelcap, as this formulation was found to enhance the beneficial properties of the actives upon oral administration. Illustrative of oily substances that may be used to provide an oily carrier include, but are not limited to, vegetable oils, e.g. olive oil, safflower oil, corn oil, sunflower oil, cotton seed oil, tsubaki oil, rice bran oil, soybean oil, sesame oil, wheat germ oil, coconut oil, peanut oil, rape seed oil and the like, fish oils, e.g., cuttlefish oil, cod oil, and the like, liver oils, e.g., shark liver oil, cod liver oil and the like, blubber oils, e.g., seal oil, blue whale oil, etc.), conchiferas oils, e.g., abalone oil, oyster oil, and the like, medicinal oily substances, e.g., castor oil, fatty acid glycerides, vitamin E, vitamin A, vitamin K, and the like, polyethylene glycol and the like, and mixtures thereof.

For parenteral administration, any type of carrier that maintains the benefits of the invention as described herein may be used. Preferably, however, and as previously mentioned, the bucyclate and/or undecanoate is suspended in an aqueous carrier suitable for injection. The water component of the aqueous carrier should constitute at least half thereof, on a weight percent basis, preferably at least about 80 wt. %, and more preferably at least about 90 wt. % of the aqueous carrier. Illustrative of a preferred parenteral formulation is one that includes up to 300 mg of the active suspended in about 1 ml of an aqueous carrier. An illustrative aqueous carrier may be prepared by combining: 1 g benzyl alcohol, 0.5 g sodium carboxylethyl cellulose 50, 0.376 g disodium hydrogen phosphate dihydrate, 1.495 g sodium dihydrogen phosphate dihydrate, with water for injection (WFI) being added to bring volume of the aqueous carrier up to 100 ml.

When formulated as an injectable, the active may be provided in any suitable form, e.g., lyophilizate, dry powder for reconstitution, a ready-to-use liquid, and in any suitable container, e.g., vial, pre-filled syringe, or the like.

The actives may also be administered transdermally. Transdermal delivery devices are well known. Illustrative transdermal devices are described in U.S. Pat. Nos. 5,635,203 and 6,024,976. When a transdermal delivery device is used, the amount of the bucyclate and/or undecanoate included in the device for therapy should range from about 5% to about 25% of the parenteral dose, and preferably from about 10% to about 20% of that dose, as set forth herein.

The following examples are provided as further illustration of the present invention, but should not be construed as limiting the invention in any respect.

Example 1

This example provides data on the androgenic potency of 7α,11β-dimethyl-17β-hydroxy-4-estren-3-one bucyclate (CDB-4386A), its free alcohol (CDB-1321D), testosterone bucyclate (CDB-1781V-1), methyltestosterone (CDB-110), testosterone (CDB-111C) and testosterone enanthate (CDB-112a) when administered orally.

Immature (about 21-day-old) Sprague-Dawley rats were orchidectomized under anesthesia, and randomly assignee to groups of ten animals for each dose level of the active undergoing testing. Each active was dissolved in 10% ethanol/sesame oil and administered by gavage (oral) each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. See, e.g., Hershberger, L. et al, Myotrophic Activity of 19-nortestosterone And Other Steroids Determined By Modified Levator And Muscle Method, *Proc. Soc. Exptl. Biol. Med.* 83 175-180 (1953). Regression analysis was performed by conventional methods using a PROPHET data management system. See, e.g., Bliss, C., The Statistics of Bioassay (Academic Press, New York, 1952); Hollister, C., *Nucleic Acids Res.* 16 1873-75 (1988). Ventral prostate weight was used as the endpoint because it is the sensitive organ to androgenic stimulation.

Figure 3:
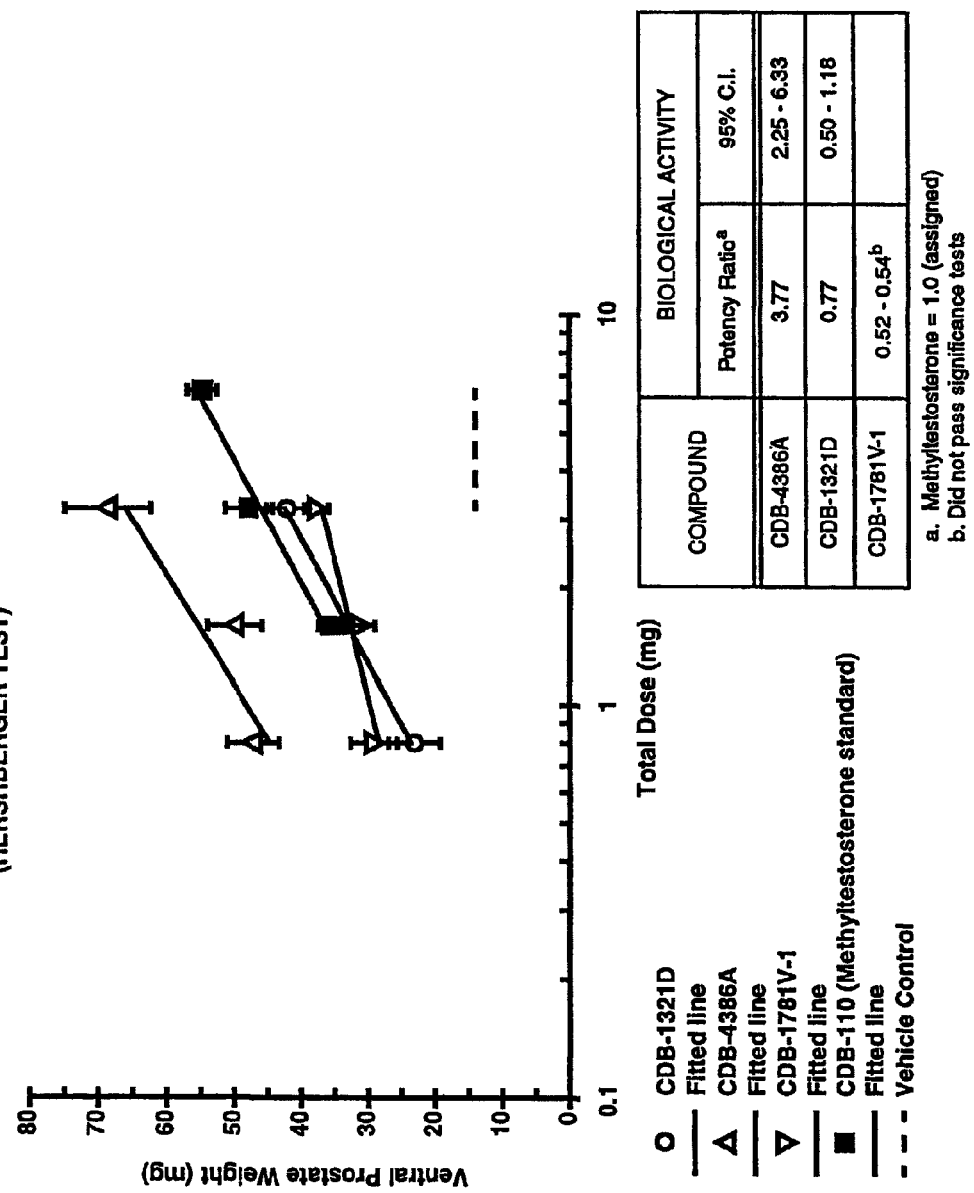
FIG. 3 is a graph comparing the androgenic potency of 7α,11β-dimethyl-17β-hydroxy-4-estren-3-one bucyclate and that of other compounds after oral administration.
Figure 4:
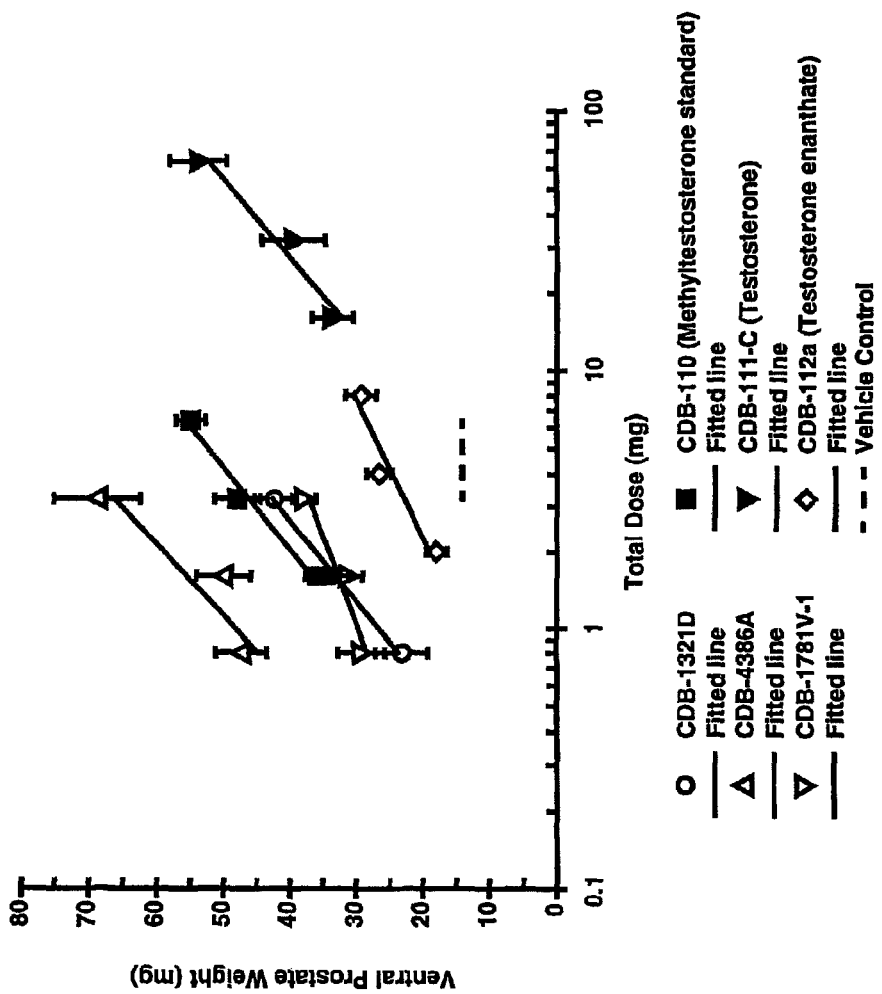
FIG. 4 is a graph comparing the androgenic potency of 7α,11β-dimethyl-17β-hydroxy-4-estren-3-one bucyclate and that of other compounds after oral administration.

The data obtained from this study is presented in graphic form in FIGS. 3 and 4. This data indicates that the oral androgenic activity of 7α,11β-dimethyl-17β-hydroxy-4-estren-3-one bucyclate is about 4 times (3.77 times, at a 95% confidence interval 2.25-6.33) as potent as methyltestosterone and at least 4 times as potent as the free alcohol (1321D), and testosterone bucyclate (1781V-1). 7α,11β-dimethyl-17β-hydroxy-4-estren-3-one bucyclate is also about 10-100 times more potent than testosterone itself (111-C) or testosterone enanthate (112a) administered orally.

Example 2

This example provides data that demonstrates the duration of activity of 7α,11β-dimethyl-17β-hydroxy-4-estren-3-one bucyclate (CDB-4386A) compared to its free alcohol (CDB-1321D), the 11α-methyl analog of 7α,11β-dimethyl-17β-hydroxy-4-estren-3-one bucyclate (CDB-4386), testosterone bucyclate (CDB-1781a, –1781V2), and testosterone enanthate (CDB-112E) when administered parenterally (by subcutaneous injection).

Immature (about 21-day-old) Sprague-Dawley rats were orchidectomized under anesthesia, and randomly assignee to groups of ten animals for each dose level of the active undergoing testing. Each active was administered by subcutaneous injection each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. Regression analysis was performed by conventional methods using a PROPHET data management system. Ventral prostate weight was used as the endpoint because it is the sensitive organ to androgenic stimulation.

Except for testosterone enanthate, each active was formulated in two different carriers: (1) an aqueous suspension and (2) in sesame oil. Testosterone enanthate was formulated using the sesame oil carrier only, because it exists as a liquid at room temperature and could not therefore be formulated as an aqueous suspension.

The carrier used to provide the aqueous suspension was formulated as follows: 1 g benzyl alcohol, 0.5 g sodium carboxylethyl cellulose 50, 0.376 g disodium hydrogen phosphate dihydrate, 1.495 g sodium dihydrogen phosphate dihydrate, with water for injection (WFI) being added to bring volume of the carrier up to 100 ml.

Each formulation was prepared at a concentration of 0.6 mg/0.2 ml. To obtain further comparative data, testosterone bucyclate was formulated in the aqueous suspension at a higher dose (1.0 mg/0.2 ml).

Figure 5:
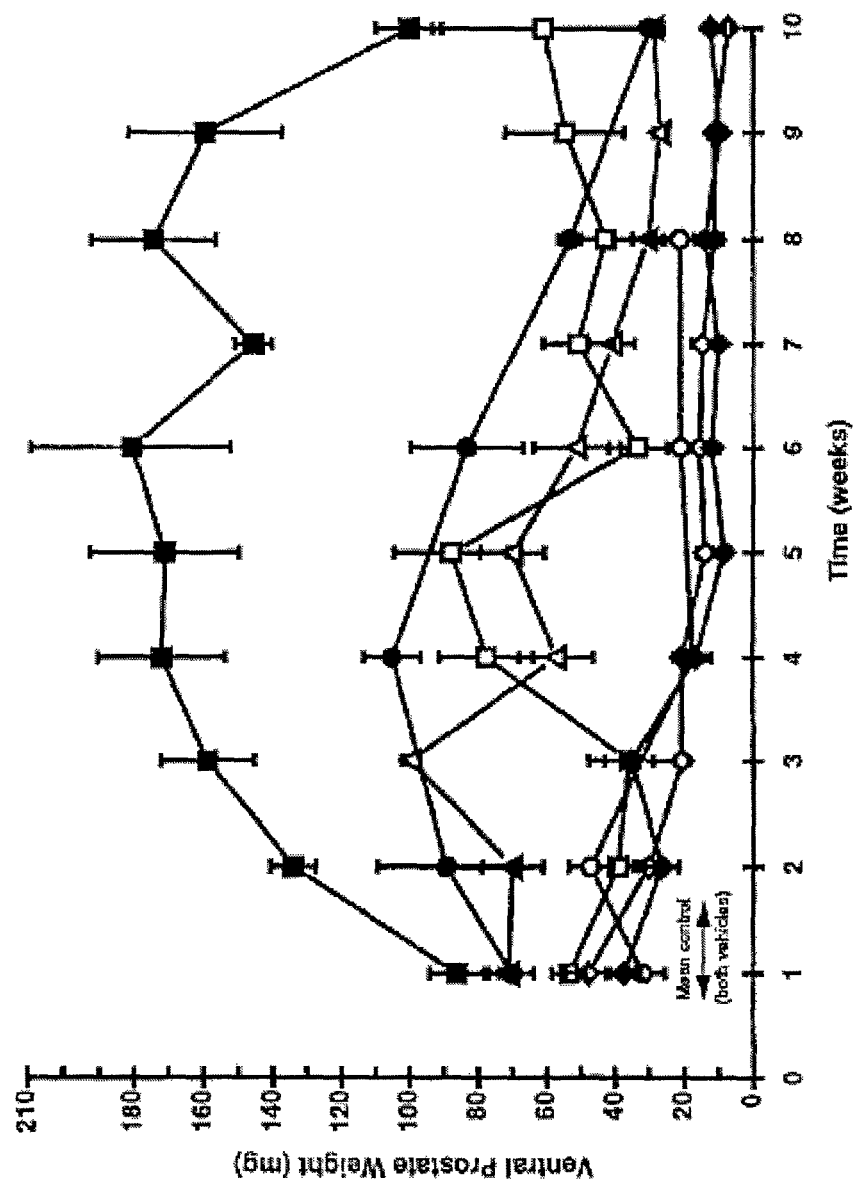
FIG. 5 is a graph comparing the duration of activity of 7α,11β-dimethyl-17β-hydroxy-4-estren-3-one bucyclate and that of other compounds after subcutaneous injection. The Y-axis depicts ventral prostate weight in castrate Sprague-Dawley rats following a single subcutaneous injection in different vehicles (n=5), -●- CDB-1781a 1.0 mg ASV [AUC=683]; -○- CDB-1781V2 0.6 mg S.O. [AUC=186]; -◆- CDB-1321D 0.6 mg ASV [AUC=460]; -■- CDB-4386A 0.6 mg ASV [AUC=1390]; -◇- CDB-1321D 0.6 mg S.O. [AUC=166]; -□- CDB-4386A 0.6 mg S.O. [AUC=157]; and -△- CDB-112E 0.6 mg S.O. [AUC=497].

The results, shown graphically in FIG. 5, substantiate the unexpected activity of 7α,11β-dimethyl-17β-hydroxy-4-estren-3-one bucyclate (CDB-4386A) as compared to other androgenic esters. The former exhibits activity in both potency and duration that far exceeds the activity exhibited by the comparative esters when administered in the same amounts, and particularly when 7α,11β-dimethyl-17β-hydroxy-4-estren-3-one bucyclate is formulated as an aqueous suspension. The activity of even CDB-4386, which may be referred to as "close" to 7α,11β-dimethyl-17β-hydroxy-4-estren-3-one bucyclate from a chemical structure perspective, nevertheless exhibits relatively low activity as compared to 7α,11β-dimethyl-17β-hydroxy-4-estren-3-one bucyclate.

Further, both the potency and long-term activity of the higher dosage of testosterone bucyclate (1.0 mg) was significantly less than that provided by the lower dosage of 7α,11β-dimethyl-17β-hydroxy-4-estren-3-one bucyclate (0.6 mg) in an aqueous suspension.

Example 3

This example illustrates the relative androgenic activity of testosterone and its derivatives.

Immature (about 21-day-old) Sprague-Dawley rats were orchidectomized under anesthesia, and randomly assignee to groups of ten animals for each dose level of the active undergoing testing. Each active was dissolved in 10% ethanol/sesame oil and administered by gavage (oral) or subcutaneous injection each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. Regression analysis was performed by conventional methods using a PROPHET data management system. Ventral prostate weight was used as the endpoint because it is the sensitive organ to androgenic stimulation.

Figure 6:
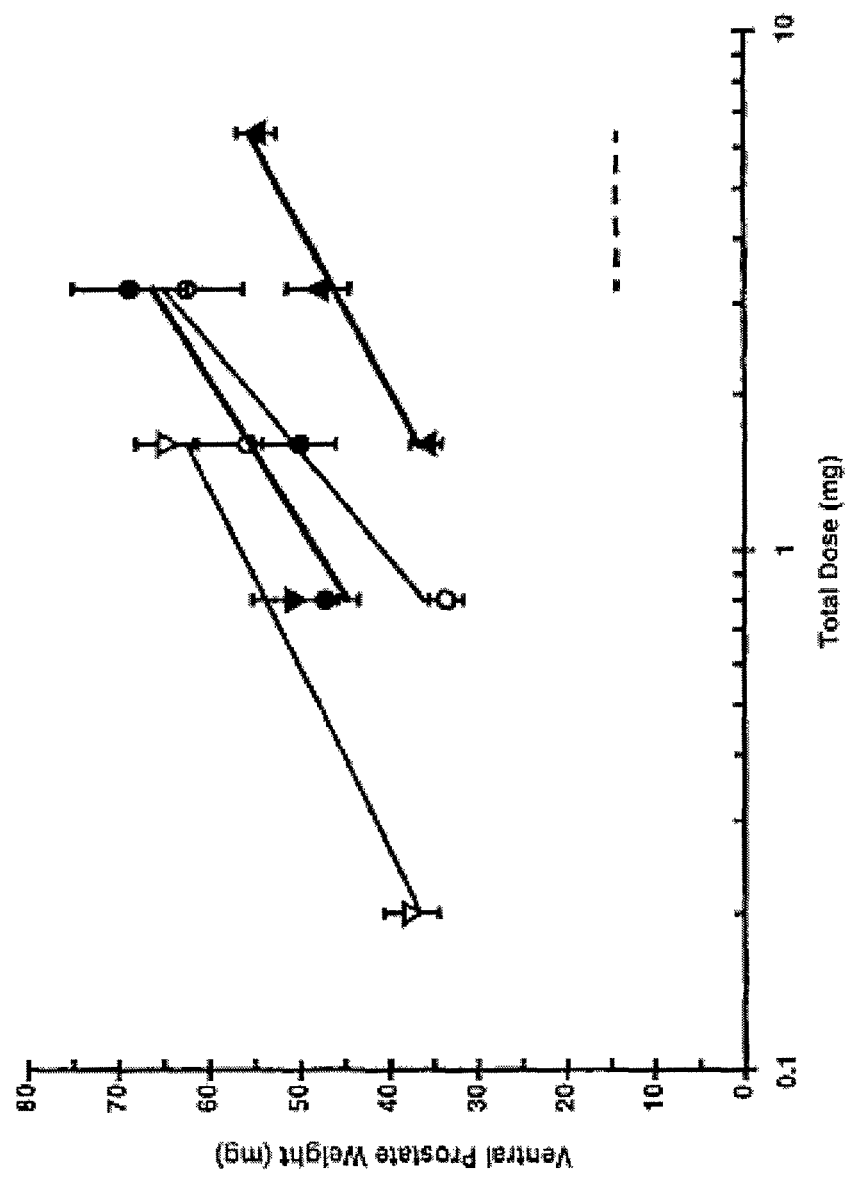
FIG. 6 is a graph comparing the androgenic potency of 7α,11β-dimethyl-17β-hydroxy-4-estren-3-one bucyclate and that of other compounds after oral and subcutaneous injection.

FIGS. 6 and 7 are graphic representations of the androgenic assays of the actives. Each data point represents the mean (n=10) and standard error of the mean (SEM) for each prostate weight for each dose level.

From the data, 7α,11β-dimethyl-17β-hydroxy-4-estren-3-one bucyclate (CDB-4386A) exhibited almost four times the oral activity of methyltestosterone (CDB-110) (3.77 times, at 95% C.I. 2.3-6.3), the current oral standard. However, 7α,11β-dimethyl-17β-hydroxy-4-estren-3-one bucyclate demonstrated only 0.4 times the activity of testosterone (CDB-111C) following subcutaneous administration (0.4 times, at 95% C.I. 0.2-0.6). The oral findings were unexpected because testosterone and its esters exhibit low activity upon oral administration.

The relatively weak activity upon subcutaneous administration was also unexpected in view of the results on the long-acting activity of 7α,11β-dimethyl-17β-hydroxy-4-estren-3-one bucyclate in Example 5. Testosterone, on the other hand, exhibited the expected level of activity after subcutaneous injection. The weak activity of the 11α-methyl analog (CDB-4415) of 7α,11β-dimethyl-17β-hydroxy-4-estren-3-one bucyclate (CDB-4386A) after subcutaneous administration indicates the importance of the stereoconfiguration of the 7α,11β-dimethyl-17β-hydroxy-4-estren-3-one bucyclate (CDB-4386A) molecule.

Although not desiring to be bound to any particular theory, the oral activity of 7α,11β-dimethyl-17β-hydroxy-4-estren-3-one bucyclate may be due to its resistance to degradation in the gastrointestinal tract and/or rapid metabolism by the liver. It is also possible that the lipophilic nature of 7α,11β-dimethyl-17β-hydroxy-4-estren-3-one bucyclate permits absorption of the active into the thoracic lymph, thereby avoiding direct entrance into the portal system and metabolism by the liver.

Further, the lack of activity experienced by 7α,11β-dimethyl-17β-hydroxy-4-estren-3-one bucyclate under subcutaneous administration may reflect the slow release, and possibly metabolism, of the active from the injection site over the relatively brief 7-day administration period. This same property, however, conveys long-acting activity on 7α,11β-dimethyl-17β-hydroxy-4-estren-3-one bucyclate after parenteral administration in an aqueous vehicle.

In addition to the foregoing, the androgenic potency and relative binding affinity to the androgen receptor of several free alcohols after subcutaneous administration of their corresponding esters was also determined. The results are presented in the following Table.

| Ester Compound | | Activity of Corresponding Alcohol | |
|---|---|---|---|
| Compound ID | Melting Point (° C.) | Relative Binding Affinity[1] | Androgenic Potency[2] |
| A | 68-69 | 91 | 8.1[3] |
| B | 129-130 | no data | 1.2 |
| C | oil | 148 | 61.1 |
| D | 108 | no data | 36.4-61.7[3] |
| E | 99-100 | 1 | no data |
| F | 130-132 | 82 | 19.3 |
| G | 134-136 | 28 | 1.0 (assigned) |

[1]From rat prostate; relative to methyltrienolone = 100% (androgenic potency = 5.0)
[2]Ventral prostate weight assay following subcutaneous administration.
[3]Did not pass one or more significance tests ($p < 0.05$)
[4]Reference compound
A: 7α-Methyl-19-nortestosterone-17β-bucyclate
B: 7α-Methyl-5α-dihydro-19-nortestosterone-17β-bucyclate
C: 7α-Methyl-14-dehydro-testosterone-17β-bucyclate
D: 7α-Methyl-D-homo-testosterone-17β-bucyclate
E: 7α,11α-Dimethyl-19-nortestosterone-17β-bucyclate
F: 7α,11β-dimethyl-17β-hydroxy-4-estren-3-one bucyclate (CDB-4386A)
G: Testosterone bucyclate The foregoing data demonstrates that the activity of a particular androgenic bucyclate ester (such as 7α,11β-dimethyl-17β-hydroxy-4-estren-3-one bucyclate, CDB-4386A) cannot be predicted on the basis of the androgenic activity of its corresponding free alcohol. More specifically, the superior activity of 7α,11β-dimethyl-17β-hydroxy-4-estren-3-one bucyclate could not have been predicted from this data.

Example 4

This example further illustrates the relative activity of various testosterone esters, including 7α,11β-dimethyl-17β-hydroxy-4-estren-3-one bucyclate, over relatively long periods of time.

Immature (about 21-day-old) Sprague-Dawley rats were orchidectomized under anesthesia, and randomly assignee to groups of 40 or more. Animals received a single subcutaneous injection of 0.6 mg of each ester in 0.2 ml of an aqueous suspending carrier and/or oily carrier (10% ethanol/ 90% sesame oil or ethyl oleate) on the date of the orchidectomy. In cases where the ester was not solid at room temperature, 10% ethanol/sesame oil or ethyl oleate was used as the carrier. In this example, the carrier used to provide the aqueous suspension was formulated as follows: 1 g benzyl alcohol, 0.5 g sodium carboxylethyl cellulose 50, 0.376 g disodium hydrogen phosphate dihydrate, 1.495 g sodium dihydrogen phosphate dihydrate, with water for injection (WFI) being added to bring volume of the carrier up to 100 ml.

Five animals from each group were sacrificed at weekly or biweekly intervals, and the ventral prostate and seminal vesicles were excised, cleaned of fat and connective tissue, blotted on moist filter paper and weighed to the nearest 0.1 mg.

Ventral prostate weight was used as the endpoint because it is the sensitive organ to androgenic stimulation. Regression analysis was performed by conventional methods using the PROPHET data management system previously identified.

FIGS. 8 and 9 are graphic representations of the androgenic assays of the actives. Each data point represents the mean (n=10) and standard error of the mean (SEM) for each prostate weight for each dose level.

FIG. 8 is a graph of the ventral prostate weights at weekly intervals over a 10 week period after the subcutaneous administration of 7α,11β-dimethyl-17β-hydroxy-4-estren-3-one bucyclate (CDB-4386A) in both oily and aqueous carriers, its 11α-methyl analog (CDB-4386) in both carriers, and testosterone enanthate (CDB-112E) in an oily carrier. 7α,11β-dimethyl-17β-hydroxy-4-estren-3-one bucyclate in the aqueous vehicle exhibited the most dramatic increase and maintenance of ventral prostate weight. The area under the curve (AUC, calculated by the trapezoidal rule), was about 3 times greater for 7α,11β-dimethyl-17β-hydroxy-4-estren-3-one bucyclate than for testosterone enanthate in sesame oil. The 11α-methyl analog was inactive in this experiment, with evaluation being discontinued 8 weeks after administration. This experiment highlights the significance of the ability to provide 7α,11β-dimethyl-17β-hydroxy-4-estren-3-one bucyclate in the form of an aqueous suspension, which provides unexpected and desirable long-term androgenic activity. This experiment also underscores the importance of the stereoconfiguration of the $C_{11}$ substituent.

FIG. 9 is a graph of the ventral prostate weights at various time intervals up to 20 weeks after administration of several different bucyclate esters: 7α,11β-dimethyl-17β-hydroxy-4-estren-3-one bucyclate (CDB-4386A), 7α-Methyl-14-dehydro-19-nortestosterone-17β-bucyclate (CDB-4327A), 7α-Methyl-19-nortestosterone-17β-bucyclate (CDB-4288), 7α-Methyl-16-dehydro-D-homo-19-nortestosterone-17β-bucyclate (CDB-4318) and 7α-Methyl-5α-dihydro-19-nortestosterone-17β-bucyclate (CDB-4289). All esters other than 7α,11β-dimethyl-17β-hydroxy-4-estren-3-one bucyclate were administered in the oily carrier because they do not exist as solids at room temperature, or possess low melting points. 7α,11β-dimethyl-17β-hydroxy-4-estren-3-one bucyclate, suspended in the aqueous carrier, exhibited the greatest AUC over the 10-week period for which this parameter was calculated. CDB-4327A demonstrated surprising stimulation of ventral prostate size over the entire 20-week observation period, however, this is one of the most active synthetic androgens presently known. The remaining actives showed relatively weak activity. This experiment can be said to demonstrate that the prediction of activity cannot be based on the structure of the active, or on the carrier used in connection with the administration of the active.

Serum samples taken from the animals at autopsy showed the presence of the free alcohol (7α,11β-dimethyl-19-nortestosterone) which decreased with time over the 10 week observation period. The results are provided in FIG. 10. 7α,11β-dimethyl-17β-hydroxy-4-estren-3-one bucyclate, suspended in the aqueous carrier, provided the highest levels of the free alcohol, and maintained these relatively high levels over the 10-week observation period.

Example 6

This example describes a preferred process for synthesizing 7α,11β-dimethyl-17β-hydroxy-4-estren-3-one bucyclate (Compound I). Reference may be made to FIG. 11.

A. Preparation of 7α-Methylestra-4,9-diene-3,17-dione (Compound 2)

Under a nitrogen flush through an inverted plastic funnel the antimony pentafluoride (110 mL, 5.79 mol) was weighed into a Teflon jar. Hydrogen fluoride (436 nL, 21.8 mol), chilled to 4° C., was first collected in a Teflon separatory funnel, then added with extreme care to the reaction vessel under a nitrogen flush. Failure to assure rapid mixing can result in an eruption. As the mixture was stirred, it was cooled to 0° C. for 20 min. 7α-methylestrone methyl ether (Compound 1, 25.0 g, 83.8 mmol) was carefully added under nitrogen. The reaction was stirred at 0° C. for 2.5 hr, after which it was slowly poured into a plastic beaker containing a mixture of saturated potassium carbonate (300 mL, 900 g/1000 mL) and ice. Additional potassium carbonate was used to adjust the pH to ca. 8. This mixture was then extracted with methylene chloride (3×) and the organic portions were washed with water and brine. After drying over sodium sulfate, the solvent was removed in vacuo to give 24.8 g of crude oil. This crude material contains Compound 2 and an isomeric by-product, 4,6-diene-dione-3,20 (Compound 3) in a 2:1 ratio. Therefore, the crude material was subjected to dry column chromatography on silica gel (63-200 mesh) eluted with 3% acetone in $CH_2Cl_2$. This gave a segment which contained 15 g of the desired product (Compound 2). After extraction, evaporation of the solvent followed by trituration with ether afforded 9.24 g of Compound 2 in 38.8% yield. The mother liquor from this material was combined with the other principle portion of the column, and was rechromatographed using the same conditions. Trituration of the segments provided an additional 0.19 g of the desired product (Compound 2). Total amount was 9.43 g in 39.6% yield; m.p. 204-205° C. (Lit. m.p.=(8). FRIR (KBr, diffuse reflectance): $v_{max}$3454, 3282, 3030, 2968, 2928, 2902, 1737, 1652, 1600, and 1580 $cm^{-1}$. NUR ($^1$H, $CDCl_3$) δ 0.859 (d, 3H, J=3.5 Hz), C7α-$CH_3$), 1.001 (s, 3H, C18-$CH_3$) and 5.726 (s, 1H, C4-CH). NMR ($^{13}$C, $CDCl_3$) δ 6 12.641, 21.835, 24.885, 25.576, 28.021, 30.626, 35, 621, 36.893, 39.416, 42.4779, 45.966, 123.259 (C-4), 126.081 (C-10)m 140.295 (C-9), 154.572 (C-5), 199.052 (C-3) and 219.633 (C-17).

B. The Preparation of 3,3-Ethylenedioxy-7α-methyl-17β-hydroxyestra-5(10),9(11)-diene (Compound 4)

A THF (500 mL) solution of the dione (Compound 2, 10.0 g, 35.16 mmol) was chilled to 0° C. and treated dropwise with a THF solution of lithium tri-tert-butoxyaluminum hydride (1.0 M/THF, 40.0 mL. 8.9 mmol). The mixture was stirred at 0° C. for 2 hr. EtOAc (10.0 mL) was added and most of the solvent was removed in vacuo. The residue was diluted with cold 0.1 N HCl and the aqueous mixture was extracted with EtOAc (3×). The EtOAc layers were washed with water and brine, combined, and dried over sodium sulfate. Evaporation of the solvent gave 10.61 g of a stable foam. The material was then dissolved in benzene (1 L). Ethylene glycol (10.0 mL) was added, followed by p-toluenesulfonic acid (500 mg). The resulting mixture was heated to reflux while draining off approximately 500 mL of benzene from the Dean-Stark trap. The mixture was cooled and diluted with saturated sodium bicarbonate solution. The benzene solution was washed with water and brine. The aqueous washes were extracted with EtOAc (2×). The combined organic extracts were dried over sodium sulfate. Evaporation of the solvent gave the 12.61 g of a stable foam. The material was chromatographed (5% acetone in $CH_2Cl_2$) to afford 10.05 g of the ketal (Compound 4) in 87% yield. NMR ($CDCl_3$) δ 0.725 (s, 3H, C18-$CH_3$), 0.727 (d, 3H, J=7.2 Hz, C7α-$CH_3$), 3.777(t, 1H, J=8.7 Hz, C17α-CH), 3.979 (m, 4H, 3-ketal) and 5.638 (m, 1H, CH=CH). MS (EI) m/z: relative intensity: 330 ($M^+$).

C. Preparation of 3,3-ethylenedioxy-7α-methyl-5α, 10α-epoxy-17β-hydroxyestra-9(11)-ene (Compound 5)

A solution of hexafluoroacetone (30.0 g, 136.2 mmol) in $CH_2Cl_2$, (150 mL) was chilled to 0° C. With vigorous stirring, 30% hydrogen peroxide (14.0 mL, 136.2 mmol) and solid disodium hydrogen phosphate (5.86 g, 41.30 mmol) was added. The resulting mixture was stirred at 0° C. for ½ hr. A solution of the ketal (Compound 4, 15.0 g 45.39 mmol) in $CH_2Cl_2$ (300 mL) was added and the mixture was stirred at 4° C. for 24 hr. The mixture was then diluted with 10% sodium sulfite solution, and subsequently extracted with $CH_2Cl_2$ (3×). The extracts were washed with water and brine, combined and dried over sodium sulfate. Evaporation of the solvent gave 16.26 g. of Compound 5. This material was used without further purification in the subsequent reaction. NMR ($CDCl_3$) δ 0.725 (s, 3H, C18-$CH_3$), 0.762 (d, 3H, J=7.2 Hz, C7α-$CH_3$), 3.758 (t, 1H, J=8.7 Hz, C17α-CH), 3.895 (d, 4H, 3-ketal) and 6.00 (m, 1H, C11=CH).

D. Preparation of 3,3-ethylenedioxy-7α,11β-dimethyl-5α,17β-dihyrdoxyestra-9-ene (Compound 6)

A solution of methylmagnesiumbromide (1.4 M THF/toluene, 210 mL, 295 mmol) was added to THF (150 mL) and copper (I) chloride (2.92 g, 29.5 mmol) was added. After stirring at room temperature for ½ hr, a solution of the epoxide (Compound 5, 16.26 g 46.99 mmol) in THF (450 mL) was added dropwise over 5 min. The mixture was stirred at room temperature for 3 hr. The mixture was diluted with saturated ammonium chloride solution and air was bubbled through the mixture for ½ hr to oxidize Cu(I) to Cu(II). The aqueous mixture was extracted with ether (3×). The ether extracts were washed with water and brine, combined, and dried over sodium sulfate. Evaporation of the solvent gave 16.70 g of a yellow semi-solid. The material was triturated with ether and the solid was filtered to afford 8.86 g of a mixture of Grignard products (7α,11β-dimethyl and 7α,11β-dimethyl, referred to as Compounds 6a and 6b, respectively). Evaporation of the filtrate gave 7.4 g of a stable foam. Total amount was 16.26 g in quantitative yield.

E. Hydrolysis of a Mixture of Compounds 6a and 6b to Isomeric Compounds 7b and 7a (as a ca. 3/7 mixture)

The solid (containing Compounds 6a and 6b) from Step D above (16.26 g, 54.2 mmol) was dissolved in acetic acid/THF/water (3:1:1, 500 mL) and heated to reflux for 2 hr. The solvent was evaporated in vacuo and the mixture was diluted with saturated sodium bicarbonate solution. The mixture was then extracted with $CH_2Cl_2$. The $CH_2Cl_2$ extracts were washed with water, brine, combined, and dried over sodium sulfate. Evaporation of the solvent gave 7.45 g. The material was chromatographed (10% acetone/methylene chloride) to afford 5.12 g of Compounds 7a and 7b (7α,11α-dimethyl and 7α,11β-dimethyl, respectively). The foam obtained in Step D was treated in the same manner to afford an additional 2.73 g of Compounds 7a and 7b after chromatography. Total amount was 7.85 g in 45.9% yield. NMR ($CDCl_3$) δ 0.747 (d, 3H, J=7 Hz, C7α-$CH_3$), 0.780 (s, 3H, C18-$CH_3$ of Compound 6b), 0.963 (s, 3H, C18-$CH_3$ of Compound 6a), 1.077 (d, 3H, J=7 Hz, C11α-$CH_3$), 1.173 (d, 3H, J=7 Hz, C11β-$CH_3$), and 3.770 (t, 1H, J=8.7 Hz, C17α-CH.

F. Preparation of 3,3-Ethyleniedioxy-7α,11-dimethyl-17β-hydroxyestra-5(10),9(11)-diene (Compound 8)

A solution of Compounds 7a/7b (2.0 g 6.65 mmol) in benzene (500 mL) was treated with ethylene glycol (5.0 mL) and p-toluenesulfonic acid (250 mg). The mixture was heated at reflux with azeotropic removal of water. Approximately 250 mL of solvent was distilled off. The mixture was cooled to room temperature and diluted with saturated sodium bicarbonate solution. The mixture was extracted with EtOAc. The EtOAc extracts were washed with water and brine, combined and dried over sodium sulfate. Evaporation of the solvent gave 2.15 g of stable foam in 93.9% yield. The material was homogeneous by TLC and less polar than the starting material. NNM ($CDCl_3$) δ 0.716 (s, 3H, C18-$CH_3$), 0.725 (d, 3H, J=7.2 Hz, C7α-$CH_3$), 1.801 (br s, 3H, C11-$CH_3$), 3.755 (t, 1H, J=8.7, C17α-CH) and 4.003 (m, 4H, 3-ketal).

G. Preparation of 7α,11β-Dimethyl-17β-hydroxyestra-4,9-diene-3-one (Compounds 7b/7a, ca. 10/1) via Hydrolysis of Compound 8

The ketal (Compound 8, 2.15 g 6.24 mmol) was dissolved in methanol (200 mL) and 10.0 mL of 10% HCl was added. The solution was heated at reflux for 18 hr. The solvent was evaporated in vacuo and the residue was diluted with saturated sodium bicarbonate solution. The aqueous mixture was extracted with $CH_2Cl_2$. The methylene chloride extracts were washed with water and brine, combined and dried over sodium sulfate. Evaporation of the solvent gave 1.89 g of a stable foam. The material was chromatographed (10% acetone in $CH_2Cl_2$) to afford 950 mg, of the 7α,11β-dimethyl compound (Compound 7b) in 50.8% yield. Also isolated 703 mg of a Compound 7a/7b mixture in which was resubjected to the ketalization and equilibrium process to yield additional material. Compound 7b: NMR ($CDCl_3$) δ 0.790 (d, 3H, J=7.2 Hz, C7α-$CH_3$), 0.963 (s, 3H, C18-$CH_3$), 1.172(d, 3H, C11β-$CH_3$), 3.186 (m, 5-lines, 1H, C11α-CH), 3.661 (t, 1H, J=8.7 Hz, C17α-CH) and 5.702 (s, 1H, C4-CH).

H. Preparation of 7α,11β-Dimethyl-17β-hydroxy-4-estren-3-one (Compound 10)

Lithium wire (253 mg, 36.45 mmol), cut into small pieces, was added to redistilled (from sodium) ammonia (300 mL) and the mixture was stirred at ammonia reflux (−35° C.) for ½ hr. The mixture was chilled to −78° C. and a solution of the dienone (Compound 7b, 3.65 g 12.15 mmol) in THF (300 mL) and t-butanol (1.16 mL, 12.15 mmol) was added dropwise. Upon completion of the addition, the reaction was stirred for 15 min before any excess lithium was destroyed with the addition of isoprene (ca. 1.0 mL) and finally, quenched with the addition of solid ammonium chloride (15 g). The ammonia was evaporated under argon gas and the mixture was diluted with 0.1 N phosphate buffer, pH=7.0. The mixture was extracted with ether. The ether extracts were washed with water and brine, combined, and dried over sodium sulfate. Evaporation of the solvent gave 3.83 g of Compound 9 as a light yellow solid in quantitative yield. The material was homogeneous by TLC and was used without further purification in the following reaction. NMR ($CDCl_3$) δ 0.812 (d, 3H, J=7.2 Hz, C7α-$CH_3$)m 0.877 (s, 3H, C18-$CH_3$), 0.903 (d, 3H, J=7.2 Hz, C11β-$CH_3$), 2.754 (br q, 2H, C4-$CH_2$—), and 3.660 (t, 1H, J=8.8 Hz, C17α-CH).

The material prepared above was dissolved in methanol (400 mL) and 10% HCl (20 mL) was added and the mixture was heated at reflux for 3 hr. The solvent was evaporated and the residue was diluted with saturated sodium bicarbonate solution. The mixture was extracted with $CH_2Cl_2$. The methylene chloride extracts were washed with water and brine, combined and dried over sodium sulfate. Evaporation of the solvent gave 3.81 g of a stable foam. The material was chromatographed (10% acetone in $CH_2Cl_2$) to afford 3.54 g of Compound 10 in 96.5% yield. The material was recrystallized from ether/hexane to give 3.14 g of Compound 10 as fine white needles in 86% yield; m.p.=155-157° C. Analysis by reverse phase HPLC on a NovaPak $C_{18}$ column eluted with 50% aqueous $CH_3CN$ at a flow rate of 1 mL per min and at λ=240 nm indicated this material to have a purity in excess of 99% FTIR (KBr, diffuse reflectance): $v_{max}$ 3470, 2950, 1663 and 1622 $cm^{-1}$. NMR (CDCl3) δ 0.770 (d, 3H, J=7.2 Hz, C7α-$CH_3$), 0.886 (s, 3H, C18-$CH_3$), 1.075 (d, 3H, J=7.2 Hz, C11β-$CH_3$), 3.626 (t, 1H, J=8.7 Hz, C17α-CH) and 5.849 (br s, 1H, C4-CH). MS (EI) m/z relative intensity: 302 ($M^+$). Analysis calculated for $C_{20}H_{30}O_2$: C, 79.42; H, 10.00. Found: C, 79.18; H, 10.00.

I. Preparation of 7α,11β-Dimethyl-17β-hydroxy-4-estren-3-one 17β-trans-4-n-butylcyclohexane carboxylate (Compound I)

Trans-4-n-Butylcyclohexanecarboxylic acid chloride (Compound 11, 2.25 g 110 mmol), dissolved in benzene (10 mL), was added to a solution of 7α,11β-Dimethyl-17β-hydroxy-4-estren-3-one (Compound 10, 608 mg, 2 mmol) in a mixture of benzene (100 mL) and pyridine (5.0 mL). The mixture was stirred overnight at room temperature. The mixture was chilled in an ice bath and diluted with 1.0 N sodium hydroxide solution. The aqueous mixture was extracted with ether. The ether extracts were washed with 1.0 N sodium hydroxide solution (2×), water and brine. The combined organic extracts were dried over sodium sulfate and evaporation of the solvent gave 1.72 g of a semi-solid. Recrystallization of the material (Compound I) from hexanes gave 765 mg of white powder in 82% yield: m.p.=130-132° C. Analysis by reverse Phase HPLC on a NovaPak $C_{18}$ column eluted with $CH_3CN$ at a flow rate of 1.25 mL per minute and at $\lambda=240$ nm showed the Compound I to be pure greater than 99%. FTIR (KBr, diffuse reflectance) $v_{max}$ 2933, 1726, 1669 and 1621 cm$^{-1}$. MR (CDCl$_3$) δ 0.779 (d, 3H, J=7.2 Hz, C7α-CH$_3$), 0.886 (t, 3H, n-butyl CH$_3$), 0.923 (s, 3H, C18-CH$_3$), 1.057 (d, 3H, J=7.2 Hz, C11β-CH$_3$), 4.545 (t, 1H, J=8.7 Hz, C17α-CH) and 5.848 (br s, 1H, C4-CH). MS (EI) m/z relative intensity: 468 (M$^+$, 6.9), 358 (65.3), 302 (12.5), 284 (20.8), 269 (6.9), 259 (12.5), 174 (62.5), 159 (26.5), 147 (19.4), 139 (25.0), 119 (18.1), 110 (75.0), 105 (8.1), 97 (36.1), 83 (100), 69 (38.9) and 55 (58.3).

Example 7

This example provides data on the androgenic potency of the undecanoate (CDB-4521A) relative to methyltestosterone (CDB-111C) when administered via subcutaneous injection.

Immature (about 21-day-old) Sprague-Dawley rats were orchidectomized under anesthesia, and randomly assignee to groups of ten animals for each dose level of the active undergoing testing. Each active was dissolved in 10% ethanol/sesame oil and administered by subcutaneous injection each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. See, e.g., Hershberger, L. et al, Myotrophic Activity of 19-nortestosterone And Other Steroids Determined By Modified Levator And Muscle Method, *Proc. Soc. Exptl. Biol. Med.* 83 175-180 (1953). Regression analysis was performed by conventional methods using a PROPHET data management system. See, e.g., Bliss, C., The Statistics of Bioassay (Academic Press, New York, 1952); Hollister, C., *Nucleic Acids Res.* 16 1873-75 (1988). Ventral prostate weight was used as the endpoint because it is the sensitive organ to androgenic stimulation.

The data obtained from this study is presented in graphic form in FIG. 13. This data indicates that the subcutaneous androgenic activity of the undecanoate (CDB-4521A) is about half that of testosterone (0.52 times, at a 95% confidence interval, 0.29-0.93) when administered in the oily carrier. This data was surprising when compared to the results obtained when the undecanoate was administered in an aqueous carrier.

Example 8

This example provides data on the androgenic potency of the undecanoate (CDB-4521) and methyltestosterone (CDB-110) when orally administered in oily or aqueous carriers.

Immature (about 21-day-old) Sprague-Dawley rats were orchidectomized under anesthesia, and randomly assignee to groups of ten animals for each dose level of the active undergoing testing. Four dosage forms were prepared. The first two forms constituted a solution of each active in 10% ethanol/sesame oil. The third and fourth dosage forms constituted a suspension of each active in an aqueous carrier (as described in Example 2, supra). These dosage forms were then administered by gavage (oral) to separate animal groups each day for seven days beginning on the date of the orchidectomy. Each carrier was also administered (alone) to separate groups of animals as a control. The animals were sacrificed 24 hours after the last dose, and the ventral prostate and seminal vesicles were excised, cleaned of fat and connective tissue, blotted on moist filter paper and weighed to the nearest 0.1 mg. See, e.g., Hershberger, L. et al, Myotrophic Activity of 19-nortestosterone And Other Steroids Determined By Modified Levator And Muscle Method, *Proc. Soc. Exptl. Biol. Med.* 83 175-180 (1953). Regression analysis was performed by conventional methods using a PROPHET data management system. See, e.g., Bliss, C., The Statistics of Bioassay (Academic Press, New York, 1952); Hollister, C., *Nucleic Acids Res.* 16 1873-75 (1988). Ventral prostate weight was used as the endpoint because it is the sensitive organ to androgenic stimulation.

The data obtained from this study is presented in graphic form in FIGS. 14 and 4. This data indicates that the oral androgenic activity of the undecanoate (CDB-4521A) in the oily carrier is about 2 times (2.36 times, at a 95% confidence interval) as potent as methyltestosterone in the same oily carrier. In contrast, oral administration of the undecanoate in the aqueous carrier described in Example 2, supra, revealed a potency about the same (0.95 times, at a 95% confidence interval, 0.36-2.5) as that of methyltestosterone in the same aqueous carrier.

Example 9

This example further illustrates the relative activity of 7α,11β-dimethyl-17β-hydroxyestr-4-en-3-one 17-undecanoate (Compound II) compared to that of testosterone enanthate (CDB-112F) over relatively long periods of time.

Immature (about 21-day-old) Sprague-Dawley rats were orchidectomized under anesthesia, and randomly assignee to groups of 40 or more. Animals received a single subcutaneous injection of 0.6 mg of the undecanoate in 0.2 ml of an aqueous suspending carrier and/or oily carrier (10% ethanol/ 90% sesame oil containing 5 mg/ml chlorobutanol as a preservative, or ethyloleate) on the date of the orchidectomy. The enanthate ester was formulated using the 10% ethanol/ sesame oil or ethyloleate carrier as a first standard, with the 10% ethanol/sesame oil carrier used as a second standard.

In this example, the carrier used to provide the aqueous suspension was formulated as follows: 1 g benzyl alcohol, 0.5 g sodium carboxylethyl cellulose 50, 0.376 g disodium hydrogen phosphate dihydrate, 1.495 g sodium dihydrogen phosphate dihydrate, with water for injection (WFI) being added to bring volume of the carrier up to 100 ml.

Five animals from each group were sacrificed at weekly or biweekly intervals, and the ventral prostate and seminal vesicles were excised, cleaned of fat and connective tissue, blotted on moist filter paper and weighed to the nearest 0.1 mg.

Ventral prostate weight was used as the endpoint because it is the sensitive organ to androgenic stimulation. Regression analysis was performed by conventional methods using the PROPHET data management system previously identified.

FIG. 15 is a graphic representation of the androgenic assays of the actives. Each data point represents the mean (n=10) and standard error of the mean (SEM) for each prostate weight for each formulation level.

More specifically, FIG. 15 is a graph of the ventral prostate weights at weekly intervals over a 10 week period after the subcutaneous administration of the undecanoate (CDB-4521) in both oily and aqueous carriers, testosterone enanthate (CDB-112F) in an oily carrier, and an oily carrier (10% ethanol/sesame oil) alone. The undecanoate in the aqueous vehicle exhibited the most dramatic increase and maintenance of ventral prostate weight. The area under the curve (AUC, calculated by the trapezoidal rule), was about 3 times greater for the undecanoate (1817 mg-weeks) than for testosterone enanthate in the oily carrier (AUC 559 mg-weeks).

This experiment highlights the significance of the ability to provide the undecanoate in the form of an aqueous suspension, which provides unexpected and desirable long-term androgenic activity. This experiment also underscores the importance of the stereoconfiguration of the $C_{11}$ substituent.

Example 10

This example describes a preferred process for synthesizing 7α,11β-dimethyl-17β-hydroxyestr-4-en-3-one 17-undecanoate (Compound II). Reference may be made to FIG. 16.

The synthesis of Compound 10 as described in Example 6 was completed. Thereafter, the undecanoate was prepared by treatment of Compound 10 with undecanoyl chloride in pyridine to provide Compound II as a white powder, in good yield.

A solution of 7α,11β-dimethyl-17β-hydroxyestr-4-en-3-one (Compound 10, 252 mg, 0.83 mmol) in a mixture of benzene (20 mL) and pyridine (2.0 mL) was treated with undecanoyl chloride (Compound 12, 500 mg, 2.44 mmol). The mixture was stirred at room temperature overnight. The mixture was then chilled in an ice bath and diluted with cold 0.1 N sodium hydroxide solution. The resulting aqueous mixture was extracted with ether. The ether extracts were washed with water and brine, combined and dried over sodium sulfate. Evaporation of the solvent gave 525 mg of an oil. The material was chromatographed using 10% acetone/$CH_2Cl_2$ to yield 398 mg of an oil. The material was recrystallized from cold pentane to afford 369.2 mg of Compound II as a white powder in 94% yield; m.p.=62-64° C. Analysis by reverse Phase HPLC on a NovaPak $C_{18}$ Column eluted with $CH_3CN$ at a flow rate of 1.0 mL per mm and at λ=240 nm showed Compound II to have a purity of at least 99.9%. FTIR (KBr, diffuse reflectance): $v_{max}$ 2914, 1733, 1678 and 1628 cm$^{-1}$. $^1$HNMR (CDCl$_3$) δ 0.782 (d, 3H, J=7.2 Hz, C7α-CH$_3$), 0.880 (t, 3H, J=9 Hz, —(CH$_2$)$_9$CH$_3$), 0.922 (s, 3H, C18-CH$_3$), 1.058 (d, 3H, J=7.2 Hz, C11β-CH$_3$), 4.565 (t, 1H, J=8.4 Hz, C17α-CH) and 5.849 (s, 1H, C4-CH=). MS (EI) m/z (relative intensity): 470 (M$^+$, 100), 302 (60), 284 (78), 259 (67), 175(89), 110 (69) and 55(96). Analysis Calculated for $C_{31}H_{50}O_3$: C, 79.10; H, 10.70. Found: C, 79.33; H, 10.91.

Any reference cited herein, including patents, patent applications, and publications, are hereby incorporated in their entireties by reference. Further, any reference herein to a component in the singular is intended to indicate and include at least one of that particular component, i.e., one or more.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

We claim as our invention:

1. A pharmaceutical composition comprising 7α,11β-dimethyl-17β-hydroxyestr-4-en-3-one 17-undecanoate and a pharmaceutically acceptable carrier, wherein a single dose of the pharmaceutical composition provides effective fertility suppression in a male patient in need thereof.

2. The pharmaceutical composition of claim 1, wherein the pharmaceutically acceptable carrier comprises an aqueous suspension vehicle.

3. The pharmaceutical composition of claim 1, wherein the composition is a parenteral formulation.

4. The pharmaceutical composition of claim 1, wherein the composition is a subcutaneous injectable formulation.

5. The pharmaceutical composition of claim 1, wherein the pharmaceutically acceptable carrier comprises an oil.

6. The pharmaceutical composition of claim 5, wherein the oil is castor oil.

7. The pharmaceutical composition of claim 1, further comprising one or more steroidal progestins or estrogens.

8. The pharmaceutical composition of claim 1, wherein a single dose of the pharmaceutical composition provides effective fertility suppression in a male patient in need thereof for at least one month.

9. The pharmaceutical composition of claim 1, wherein a single dose of the pharmaceutical composition provides effective fertility suppression in a male patient in need thereof for at least six weeks.

10. The pharmaceutical composition of claim 1, wherein a single dose of the pharmaceutical composition provides effective fertility suppression in a male patient in need thereof for at least two months.

11. The pharmaceutical composition of claim 1, wherein a single dose of the pharmaceutical composition provides effective fertility suppression in a male patient in need thereof for at least three months.

12. A pharmaceutical composition comprising 7α,11β-dimethyl-17β-hydroxyestr-4-en-3-one 17-undecanoate and a pharmaceutically acceptable carrier, wherein a single dose of the pharmaceutical composition provides effective hormone therapy in a patient in need thereof.

13. The pharmaceutical composition of claim 12, wherein the pharmaceutically acceptable carrier comprises an aqueous suspension vehicle.

14. The pharmaceutical composition of claim 12, wherein the composition is a parenteral formulation.

15. The pharmaceutical composition of claim 12, wherein the composition is a subcutaneous injectable formulation.

16. The pharmaceutical composition of claim 12, wherein the pharmaceutically acceptable carrier comprises an oil.

17. The pharmaceutical composition of claim 16, wherein the oil is castor oil.

18. The pharmaceutical composition of claim 12, further comprising one or more steroidal progestins or estrogens.

19. The pharmaceutical composition of claim 12, wherein a single dose of the pharmaceutical composition provides effective hormone therapy in a patient in need thereof for at least one month.

20. The pharmaceutical composition of claim 12, wherein a single dose of the pharmaceutical composition provides effective hormone therapy in a patient in need thereof for at least six weeks.

21. The pharmaceutical composition of claim 12, wherein a single dose of the pharmaceutical composition provides effective hormone therapy in a patient in need thereof for at least two months.

22. The pharmaceutical composition of claim 12, wherein a single dose of the pharmaceutical composition provides effective hormone therapy in a patient in need thereof for at least three months.

* * * * *